(12) United States Patent
Pravong et al.

(10) Patent No.: US 9,522,265 B2
(45) Date of Patent: *Dec. 20, 2016

(54) TROCAR CANNULA ASSEMBLY WITH LOW PROFILE INSERTION CONFIGURATION AND METHOD OF MANUFACTURE

(71) Applicant: Applied Medical Resources Corporation, Rancho Santa Margarita, CA (US)

(72) Inventors: Boun Pravong, Rancho Santa Margarita, CA (US); Kennii Pravongviengkham, Rancho Santa Margarita, CA (US); Eduardo Bolanos, Rancho Santa Margarita, CA (US); Joel B. Velasco, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 234 days.

This patent is subject to a terminal disclaimer.

(21) Appl. No.: 14/209,161

(22) Filed: Mar. 13, 2014

(65) Prior Publication Data

US 2014/0276945 A1  Sep. 18, 2014

Related U.S. Application Data

(60) Provisional application No. 61/792,285, filed on Mar. 15, 2013.

(51) Int. Cl.
*A61B 1/00* (2006.01)
*A61M 39/02* (2006.01)
(Continued)

(52) U.S. Cl.
CPC .......... *A61M 39/02* (2013.01); *A61B 17/3417* (2013.01); *A61M 39/0247* (2013.01);
(Continued)

(58) Field of Classification Search
CPC ..... A61B 17/3417; A61B 19/201; A61B 1/32; A61B 2017/3454; A61B 1/00; A61M 39/02; A61M 39/0247
See application file for complete search history.

(56) References Cited

U.S. PATENT DOCUMENTS

| 2,185,927 A | 2/1940 | Shelanski |
| 2,687,131 A | 8/1954 | Raiche |

(Continued)

FOREIGN PATENT DOCUMENTS

| DE | 41 04 586 | 8/1992 |
| EP | 0 530 595 | 3/1993 |

(Continued)

OTHER PUBLICATIONS

The International Bureau of WIPO, International Preliminary Report on Patentability, dated Sep. 24, 2015, for International Application No. PCT/US2014/026103.

(Continued)

*Primary Examiner* — Victor Nguyen
(74) *Attorney, Agent, or Firm* — John F. Heal

(57) ABSTRACT

A cannula assembly having a retention member and a method of manufacture of the cannula assembly is provided. The cannula assembly includes a cannula and a sleeve disposed around the cannula from a proximal end to a distal end. The sleeve can include a balloon formed by a stretch blow molding process following local heating once advanced over the cannula. Once formed, the balloon can be conditioned to constrict against the cannula. A conditioning (Continued)

aid can be advanced over the balloon when it is still formable to constrict the balloon against the cannula.

9 Claims, 19 Drawing Sheets

(51) Int. Cl.
*A61B 17/34* (2006.01)
*A61B 17/00* (2006.01)

(52) U.S. Cl.
CPC ............... *A61B 2017/00526* (2013.01); *A61B 2017/3454* (2013.01); *A61B 2017/3486* (2013.01); *A61B 2017/3492* (2013.01); *A61M 2039/0255* (2013.01); *A61M 2039/0261* (2013.01); *A61M 2039/0279* (2013.01)

(56) References Cited

U.S. PATENT DOCUMENTS

| | | |
|---|---|---|
| 3,039,468 A | 6/1962 | Price |
| 3,044,468 A | 7/1962 | Birtwell |
| 3,154,077 A | 10/1964 | Cannon |
| 3,253,594 A | 5/1966 | Matthews et al. |
| 3,459,175 A | 8/1969 | Miller |
| 3,484,121 A | 12/1969 | Quinton |
| 3,634,924 A | 1/1972 | Blake et al. |
| 3,817,251 A | 6/1974 | Hasson |
| 3,952,742 A | 4/1976 | Taylor |
| 3,962,519 A | 6/1976 | Rusch et al. |
| 3,970,090 A | 7/1976 | Loiacono |
| 3,971,385 A | 7/1976 | Corbett |
| 4,077,412 A | 3/1978 | Mossun |
| 4,496,345 A | 1/1985 | Hasson |
| 4,555,242 A | 11/1985 | Saudagar |
| 4,601,710 A | 7/1986 | Moll |
| 4,649,904 A | 3/1987 | Krauter et al. |
| 4,655,752 A | 4/1987 | Honkanen et al. |
| 4,670,008 A | 6/1987 | Von Albertini |
| 4,809,679 A | 3/1989 | Shimonaka et al. |
| 4,834,721 A | 5/1989 | Onohara et al. |
| 4,861,334 A | 8/1989 | Nawaz |
| 4,946,464 A | 8/1990 | Pevsner |
| 5,002,557 A | 3/1991 | Hasson |
| 5,009,643 A | 4/1991 | Reich et al. |
| 5,098,388 A | 3/1992 | Kulkashi et al. |
| 5,100,390 A | 3/1992 | Lubeck et al. |
| 5,103,804 A | 4/1992 | Abele et al. |
| 5,122,122 A | 6/1992 | Allgood |
| 5,147,316 A | 9/1992 | Castillenti |
| 5,176,697 A | 1/1993 | Hasson et al. |
| 5,203,773 A | 4/1993 | Green |
| 5,226,890 A | 7/1993 | Ianniruberto et al. |
| D338,270 S | 8/1993 | Stephens et al. |
| 5,257,975 A | 11/1993 | Foshee |
| 5,271,380 A | 12/1993 | Riek et al. |
| 5,273,545 A | 12/1993 | Hunt et al. |
| 5,279,567 A | 1/1994 | Ciaglia et al. |
| 5,290,249 A | 3/1994 | Foster |
| 5,300,036 A | 4/1994 | Mueller et al. |
| 5,309,896 A | 5/1994 | Moll et al. |
| 5,330,497 A | 7/1994 | Freitas et al. |
| 5,331,975 A | 7/1994 | Bonutti |
| 5,354,270 A | 10/1994 | Wilk et al. |
| 5,355,897 A | 10/1994 | Pietrafitta et al. |
| 5,361,752 A | 11/1994 | Moll et al. |
| 5,370,134 A | 12/1994 | Chin et al. |
| D354,562 S | 1/1995 | Medema |
| 5,383,889 A | 1/1995 | Warner et al. |
| 5,395,333 A | 3/1995 | Brill |
| 5,402,772 A | 4/1995 | Moll et al. |
| 5,403,336 A | 4/1995 | Kieturakis et al. |
| 5,425,357 A | 6/1995 | Moll et al. |
| 5,431,173 A | 7/1995 | Chin et al. |
| 5,437,646 A | 8/1995 | Hunt et al. |
| 5,445,615 A | 8/1995 | Yoon |
| 5,445,644 A | 8/1995 | Pietrafitta et al. |
| 5,450,843 A | 9/1995 | Moll et al. |
| 5,454,367 A | 10/1995 | Moll et al. |
| 5,464,449 A | 11/1995 | Ryan et al. |
| 5,465,711 A | 11/1995 | Moll et al. |
| 5,468,248 A | 11/1995 | Chin et al. |
| 5,472,429 A | 12/1995 | Yoon |
| 5,478,329 A | 12/1995 | Ternamian |
| 5,496,280 A | 3/1996 | Vandenbroek et al. |
| 5,501,653 A | 3/1996 | Chin |
| 5,503,631 A | 4/1996 | Onishi et al. |
| 5,505,689 A | 4/1996 | Kramer et al. |
| 5,512,051 A | 4/1996 | Wang et al. |
| 5,514,075 A | 5/1996 | Moll et al. |
| 5,514,096 A | 5/1996 | Hiejima et al. |
| 5,520,609 A | 5/1996 | Moll et al. |
| 5,522,790 A | 6/1996 | Moll et al. |
| 5,527,264 A | 6/1996 | Moll et al. |
| 5,531,688 A | 7/1996 | Hiejima et al. |
| 5,531,856 A | 7/1996 | Moll et al. |
| 5,540,675 A | 7/1996 | Hasson |
| 5,562,603 A | 10/1996 | Moll et al. |
| 5,562,684 A | 10/1996 | Kammerer |
| 5,569,165 A | 10/1996 | Chin et al. |
| 5,575,759 A | 11/1996 | Moll et al. |
| 5,591,191 A | 1/1997 | Kieturakis |
| 5,601,559 A | 2/1997 | Melker et al. |
| 5,630,805 A | 5/1997 | Ternamian |
| 5,632,761 A | 5/1997 | Smith et al. |
| 5,634,883 A | 6/1997 | Chin et al. |
| 5,643,178 A | 7/1997 | Moll et al. |
| 5,649,909 A | 7/1997 | Cornelius |
| 5,656,013 A | 8/1997 | Yoon |
| 5,658,272 A | 8/1997 | Hasson |
| 5,676,636 A | 10/1997 | Chin |
| 5,690,607 A | 11/1997 | Chin et al. |
| 5,697,913 A | 12/1997 | Sierocuk et al. |
| 5,697,946 A | 12/1997 | Hopper et al. |
| 5,704,372 A | 1/1998 | Moll et al. |
| 5,713,869 A | 2/1998 | Morejon |
| 5,716,327 A | 2/1998 | Warner et al. |
| 5,722,983 A | 3/1998 | Van Der Weegen |
| 5,722,986 A | 3/1998 | Smith et al. |
| 5,728,119 A | 3/1998 | Smith et al. |
| 5,738,629 A | 4/1998 | Moll et al. |
| 5,743,850 A | 4/1998 | Moll et al. |
| 5,743,851 A | 4/1998 | Moll et al. |
| 5,746,762 A | 5/1998 | Bass |
| 5,772,632 A | 6/1998 | Forman |
| 5,779,697 A | 7/1998 | Glowa et al. |
| 5,779,728 A | 7/1998 | Lunsford et al. |
| 5,795,332 A | 8/1998 | Lucas et al. |
| 5,803,901 A | 9/1998 | Chin et al. |
| 5,820,555 A | 10/1998 | Watkins, III et al. |
| 5,830,232 A | 11/1998 | Hasson |
| 5,836,871 A | 11/1998 | Wallace et al. |
| 5,836,913 A | 11/1998 | Orth et al. |
| 5,855,566 A | 1/1999 | Dunlap |
| 5,865,728 A | 2/1999 | Moll et al. |
| 5,895,351 A | 4/1999 | Nottage et al. |
| 5,924,424 A | 7/1999 | Stevens et al. |
| 5,925,058 A | 7/1999 | Smith et al. |
| 5,935,098 A | 8/1999 | Blaisdell et al. |
| 5,951,588 A | 9/1999 | Moenning |
| 5,957,888 A | 9/1999 | Hinchliffe |
| 5,961,490 A | 10/1999 | Adams |
| 5,968,065 A | 10/1999 | Chin |
| 5,984,896 A | 11/1999 | Boyd |
| 5,993,471 A | 11/1999 | Riza et al. |
| 6,033,379 A | 3/2000 | Barra et al. |
| 6,102,928 A | 8/2000 | Bonutti |
| 6,203,526 B1 | 3/2001 | McBeth et al. |
| 6,203,558 B1 | 3/2001 | Dusbabek et al. |
| 6,224,608 B1 | 5/2001 | Ciccolella et al. |
| 6,238,373 B1 | 5/2001 | De la Torre et al. |
| 6,264,670 B1 | 7/2001 | Chin |
| 6,306,144 B1 | 10/2001 | Sydney et al. |

(56) References Cited

U.S. PATENT DOCUMENTS

| | | |
|---|---|---|
| 6,344,038 B1 | 2/2002 | Weber |
| 6,355,029 B1 | 3/2002 | Joye et al. |
| 6,361,543 B1 | 3/2002 | Chin et al. |
| 6,402,720 B1 | 6/2002 | Miller et al. |
| 6,432,085 B1 | 8/2002 | Stellon et al. |
| 6,451,041 B1 | 9/2002 | Moenning et al. |
| 6,458,138 B1 | 10/2002 | Sydney et al. |
| 6,485,410 B1 | 11/2002 | Loy |
| 6,524,283 B1 | 2/2003 | Hopper et al. |
| 6,589,167 B1 | 7/2003 | Shimomura et al. |
| 6,605,037 B1 | 8/2003 | Moll et al. |
| 6,626,918 B1 | 9/2003 | Ginn et al. |
| 6,632,197 B2 | 10/2003 | Lyon |
| 6,638,265 B1 | 10/2003 | Ternamian |
| 6,648,873 B2 | 11/2003 | Arenberg et al. |
| 6,733,439 B2 | 5/2004 | Zigler |
| 6,808,492 B2 | 10/2004 | Snyder |
| 6,811,546 B1 | 11/2004 | Calllas et al. |
| 6,814,713 B2 | 11/2004 | Aboul-Hosn et al. |
| 6,908,454 B2 | 6/2005 | McFairlane |
| 6,908,462 B2 | 6/2005 | Joye et al. |
| 6,913,601 B2 | 7/2005 | St. Goar et al. |
| 6,923,827 B2 | 8/2005 | Campbell et al. |
| 7,033,384 B2 | 4/2006 | Gannoe et al. |
| 7,052,454 B2 | 5/2006 | Taylor et al. |
| 7,052,507 B2 | 5/2006 | Wakuda et al. |
| 7,153,319 B1 | 12/2006 | Haberland et al. |
| 7,235,064 B2 | 6/2007 | Hopper et al. |
| 7,300,448 B2 | 11/2007 | Criscuolo et al. |
| 7,691,089 B2 | 4/2010 | Gresham |
| 8,287,503 B2 | 10/2012 | Albrecht |
| 8,382,707 B2 | 2/2013 | Albrecht et al. |
| 2003/0114878 A1 | 6/2003 | Diederich et al. |
| 2003/0139758 A1 | 7/2003 | Hopper et al. |
| 2003/0236544 A1 | 12/2003 | Lunsford et al. |
| 2004/0098045 A1 | 5/2004 | Grafton et al. |
| 2004/0111061 A1 | 6/2004 | Curran |
| 2004/0116894 A1 | 6/2004 | DeLegge |
| 2004/0138702 A1 | 7/2004 | Peartree et al. |
| 2004/0181273 A1 | 9/2004 | Brasington et al. |
| 2004/0230218 A1 | 11/2004 | Criscuolo et al. |
| 2004/0243167 A1 | 12/2004 | Tanaka et al. |
| 2005/0004592 A1 | 1/2005 | Criscuolo |
| 2005/0113856 A1 | 5/2005 | Epstein et al. |
| 2005/0165432 A1* | 7/2005 | Heinrich ............... 606/167 |
| 2005/0177104 A1 | 8/2005 | Conway |
| 2005/0192615 A1 | 9/2005 | De la Torre et al. |
| 2005/0209607 A1 | 9/2005 | Lipchitz et al. |
| 2005/0278024 A1 | 12/2005 | Murphy et al. |
| 2006/0047293 A1 | 3/2006 | Haberland et al. |
| 2006/0079838 A1 | 4/2006 | Walker et al. |
| 2006/0079918 A1 | 4/2006 | Creston |
| 2006/0079922 A1 | 4/2006 | Creston |
| 2006/0135973 A1 | 6/2006 | Hawkins |
| 2006/0276769 A1* | 12/2006 | Domkowski et al. ........ 604/408 |
| 2006/0282047 A1 | 12/2006 | Smith |
| 2007/0162067 A1 | 7/2007 | Lunsford et al. |
| 2007/0213675 A1* | 9/2007 | Albrecht et al. ............. 604/264 |
| 2008/0200943 A1 | 8/2008 | Barker et al. |
| 2008/0306442 A1 | 12/2008 | Bardsley et al. |
| 2009/0221961 A1 | 9/2009 | Tal et al. |
| 2011/0144583 A1 | 6/2011 | Matov et al. |
| 2013/0184736 A1 | 7/2013 | Aman et al. |

FOREIGN PATENT DOCUMENTS

| | | |
|---|---|---|
| EP | 1 097 675 | 5/2001 |
| RU | 2234872 | 8/2004 |
| WO | WO 92/21291 | 12/1992 |
| WO | WO 92/21292 | 12/1992 |
| WO | WO 92/21294 | 12/1992 |
| WO | WO 92/21295 | 12/1992 |
| WO | WO 92/21298 | 12/1992 |
| WO | WO 97/06732 | 2/1997 |
| WO | WO 9713464 | 4/1997 |
| WO | WO 2004/032756 | 4/2004 |
| WO | WO 2004/047656 | 6/2004 |

OTHER PUBLICATIONS

The International Bureau of WIPO, International Preliminary Report on Patentability for International Application No. PCT/US2008/053298 mailed Sep. 17, 2009.

The International Bureau of WIPO, International Preliminary Report on Patentability for International Application No. PCT/US2007/063728 dated Sep. 16, 2008.

European Patent Office, Written Opinion of the International Searching Authority and International Search Report for International Application No. PCT/US2007/063728, mailed Sep. 4, 2007.

International Searching Authority (US), The International Search Report and the Written Opinion of the International Searching Authority, for International Application No. PCT/US08/53298, mailed Aug. 19, 2008.

The International Bureau of WIPO, International Preliminary Report on Patentability for International Application No. PCT/US2009/035810, dated Sep. 7, 2010, entitled "Balloon Trocar Advanced Fixation".

European Patent Office, Extended European Search Report for European Application No. EP 09 71 7684 dated Jun. 16, 2011.

Nternational Searching Authority/US, The International Search Report and Written Opinion for International Application No. PCT/US09/035810, mailed Apr. 15, 2009, entitled "Balloon Trocar Advanced Fixation".

U.S. Pat. No. 8,147,453, issued Apr. 3, 2012, entitled Balloon Trocar, and its associated filed history.

U.S. Appl. No. 11/683,821, filed Mar. 8, 2007, entitled Balloon Trocar, and its associated filed history.

U.S. Appl. No. 13/438,566, filed Apr. 3, 2012, entitled Balloon Trocar, and its associated filed history.

U.S. Appl. No. 12/396,624, filed Mar. 3, 2009, entitled Balloon Trocar Advanced Fixation, and its associated filed history.

Cooper Surgical, Balloon Cannula, 2014 Cooper Surgical, Inc.

International Searching Authority, The International Search Report and the Written Opinion of the International Search Authority for International Application No. PCT/US2014/026103, titled "Insertion Cannula Assembly with Low Profile Configuration Method of Manufacture", filed Mar. 13, 2014.

* cited by examiner

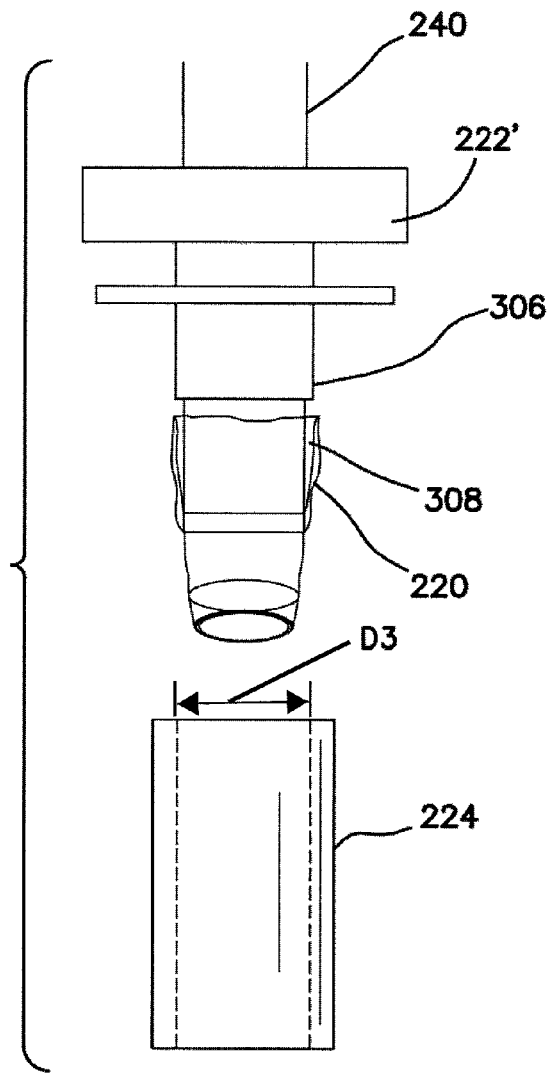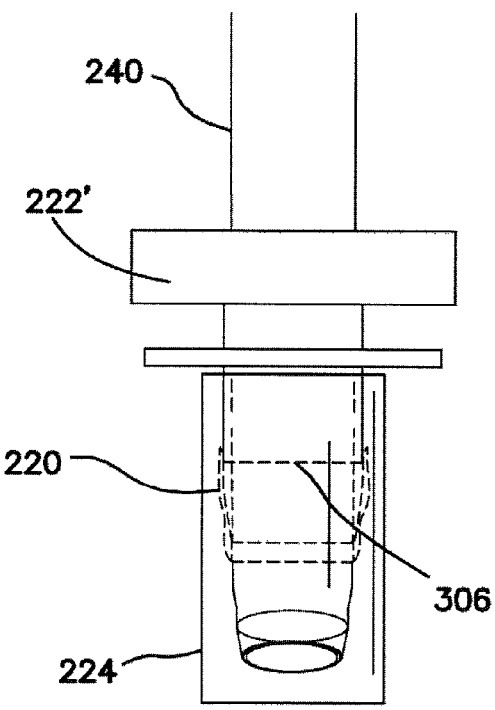
FIG. 25
FIG. 26

TROCAR CANNULA ASSEMBLY WITH LOW PROFILE INSERTION CONFIGURATION AND METHOD OF MANUFACTURE

CROSS REFERENCE TO RELATED APPLICATIONS

This application claims the benefit of U.S. Provisional Patent Application Ser. No. 61/792,285, entitled "TROCAR CANNULA ASSEMBLY WITH LOW PROFILE INSERTION CONFIGURATION AND METHOD OF MANUFACTURE," filed on Mar. 15, 2013. The entirety of this prior application is hereby incorporated herein by reference.

BACKGROUND OF THE INVENTION

Field of the Invention

This application relates generally to surgical access systems and methods of manufacturing such systems and, more specifically, to balloon trocars with retention components and methods of manufacturing the same.

Description of the Related Art

Surgical access systems such as trocar systems facilitate minimally invasive surgery across a body wall and within a body cavity. For example, in abdominal surgery, trocars provide a working channel across the abdominal wall to facilitate the use of instruments within the abdominal cavity. Trocar systems typically include a cannula, which provides the working channel, and an obturator that is used to place the cannula across a body wall, such as the abdominal wall. The obturator is inserted into the working channel of the cannula and pushed through the body wall with a penetration force of sufficient magnitude to result in penetration of the body wall. Alternatively, the cannula with an obturator is passed through an incision formed by the "Hasson," or cut-down, technique, which includes incremental incisions through the body wall until the body wall is incised through its entire thickness. Once the cannula has traversed the body wall, the obturator can be removed.

With the cannula in place in the body wall, various instruments may be inserted through the cannula into the body cavity. One or more cannulae may be used during a procedure. During the procedure, the surgeon manipulates the instruments in the cannulae, sometimes using more than one instrument at a time. The manipulation of an instrument by a surgeon may cause frictional forces between the instrument and the cannula in which the instrument is inserted. These frictional forces may result in movement of the cannula in an inward or outward direction within the body wall. If the cannula is not fixed in place, the proximal or distal motions of the instruments through the cannula may potentially cause the cannula to slip out of the body wall or to protrude further into the body cavity, possibly leading to injury to the patient.

The surfaces of the cannula associated with a trocar are generally smooth. The smoothness of a cannula surface makes placement of the cannula through a body wall relatively easy and safe. However, a smooth cannula may not have the desired retention characteristics once the cannula has been placed through a body wall. This smoothness and ease of placement may present problems as instruments and specimens are removed from a body cavity through the cannula and the associated seal systems of the trocar. It is highly desirable for a cannula to remain fixed in an appropriate position once placed. Additionally, if the Hasson technique is used, the incision may be larger than the cannula that may be placed through the incision. Therefore, it is desirable to provide a means to seal the incision site after the cannula has been inserted in order to insufflate a patient.

Various solutions to the issue of trocar-cannula fixation or stabilization have been attempted. These attempts include an inflatable balloon attached to the distal portion of the cannula with a thick foam bolster proximal to the insertion point into the body wall, raised threads or raised rings associated with the outer surface of the cannula, mechanically deployable enlarging portions arranged at the distal end of a cannula and suture loops or hooks associated with the proximal end of the trocar. These attempts have provided some degree of fixation or stabilization, but they have often led to cannulae having a relatively large outside diameter. Further, the thick foam bolster associated with balloon trocars has reduced the usable length of the cannula. There remains a need for a cannula fixation or stabilization device that includes a sleeve having retention means that minimize the increase in diameter. Additionally, the cannula fixation or stabilization device may include a lower profile and increase the working length of the cannula.

Methods for achieving the above comprise inflatable toroidal balloons that are sized larger than the cannula associated with the access device and usually disposed at or toward the distal end thereof. During insertion of the access channel through a body wall, the balloon is deflated. The balloon is inflated when the access channel is within the body cavity and properly placed. Most of the balloons associated with access devices are distensible or made of an elastic material. In some cases the balloons are made of a non-distensible or non-elastic material.

SUMMARY OF THE INVENTION

A balloon trocar, in various embodiments in accordance with the present invention, can be used in general, abdominal, gynecological and thoracic minimally invasive surgical procedures to establish a path of entry or to gain access through the tissue planes and/or potential spaces for endoscopic instruments. In various embodiments, a balloon trocar comprises an inflatable balloon at the distal end of a trocar cannula and a bolster toward the proximal end of the cannula. To use the balloon trocar, a surgeon inserts the balloon trocar into the body cavity such that the balloon section of the cannula is within the cavity, e.g., for abdominal surgery, beyond the peritoneal lining and within the abdominal cavity. The balloon is inflated and the bolster located toward the proximal end of the cannula is moved distally along the length of the cannula in order to compress the balloon against the inside of the body wall and seal the incision. With the bolster against the outer surface of the body wall, the balloon is maintained in compression against the inner surface of the body wall. In this manner, a seal is created between the balloon and the body wall, thereby allowing a surgeon to insufflate a patient. The balloon may remain inflated during the duration of a laparoscopic surgery, which may last up to four hours or more.

An elastic balloon is formed as a small inflatable structure. When deflated, an elastic balloon assumes a natural "low-profile" condition and conforms to the outer surface of the access channel or cannula. A non-elastic balloon is formed to assume a preferred maximum size and shape in a natural condition. Therefore, there exists a surplus of non-elastic balloon material when the balloon is deflated. As such, non-elastic balloon structures associated with an access channel that closely conforms to the exterior of the access channel and minimizes the interference between the deflated balloon and the tissue of a body wall during the insertion of the access device are desirable.

In accordance with various embodiments of the present invention, a balloon trocar is provided in which the balloon or retention component reduces insertion force of the balloon trocar. In one embodiment, a balloon or expandable membrane positioned on or near the distal end of the cannula of the trocar is void or without or having little air within the balloon and is folded proximally or away from the direction in which the trocar is to be inserted into the body cavity. The evacuation of air and folding of the balloon reduces resistance and the insertion force used to insert the cannula within the body cavity without reducing balloon strength to maintain retention by the balloon and integrity of the seal and the balloon itself. Additionally, such a balloon permits the utilization of a reduced insertion force relative to the insertion force of a non-folded balloon. A reduced insertion force permits a more controlled entry of the trocar into the body cavity. A more controlled entry reduces inadvertent and undesirable contact with organs, tissue, other inserted devices or ports within the body cavity. Also, a reduced insertion force reduces potential trauma to the incision or entry site as less force is applied to the site as the trocar is being inserted into the body cavity.

In various embodiments, an access channel or cannula that is associated with a surgical access device or trocar is provided. The cannula is sized and configured to receive a retention and stabilizing balloon along the distal portion. A non-elastic balloon made of polyolefin, nylon, polyester, polyethylene or the like is placed along a location upon the cannula. The deflated non-elastic balloon is maintained in the lowest profile condition for insertion through a body wall. The balloon conforms very closely the profile of the cannula. A folded balloon condition is maintained.

In certain embodiments, a cannula assembly is provided. The cannula assembly comprises a cannula and a sleeve. The cannula has a proximal end, a distal end opposite the proximal end, and a lumen extending from the proximal end to the distal end along a longitudinal axis. The lumen is configured to receive a surgical instrument therein. The cannula comprises a generally tubular cannula body and an annular recess. The generally tubular cannula body has an exterior surface and a first outer diameter. The annular recess is formed in the exterior surface of the cannula body adjacent the distal end of the cannula. The annular recess is transverse to the longitudinal axis. The annular recess has a second outer diameter smaller than the first outer diameter of the cannula body. The sleeve has a proximal end and a distal end. The sleeve is disposed around the cannula from adjacent the proximal end of the cannula to the annular recess. The sleeve comprises an elongate tubular body and a balloon positioned distal the elongate tubular body. In some embodiments, the sleeve further comprises a chamfered leading edge at the distal end of the sleeve. In some embodiments, the annular recess has a textured surface adapted to receive an adhesive. In some embodiments, the cannula assembly further comprises a conditioning aid removably disposed around the balloon. The conditioning aid is sized to compress the balloon proximally along the exterior surface of the generally tubular cannula body in a snug fit defining a low diameter insertion profile.

In certain embodiments, a method of making a cannula assembly having an inflatable balloon is provided. The method comprises positioning a generally tubular sleeve over a cannula, bonding the sleeve to the cannula, locally heating a predetermined length of the tubular sleeve, applying a source of inflation fluid to the tubular sleeve to form a balloon, and conditioning the balloon to constrict against the cannula. The generally tubular sleeve has a proximal end and a distal end. The cannula has a proximal end and a distal end and comprises an elongate cannula body with an annular groove formed in the cannula body at the distal end of the cannula. Bonding the sleeve to the cannula comprises bonding the proximal end and the distal end of the sleeve to the cannula. Locally heating the tubular sleeve comprises locally heating a predetermined length of the tubular sleeve adjacent the distal end of the tubular sleeve. The balloon is formed adjacent the distal end of the tubular sleeve. After forming the balloon and while the balloon retains residual heat from the local heating, the balloon is conditioned to constrict against the cannula.

BRIEF DESCRIPTION OF THE DRAWINGS

FIG. 25 schematically illustrates a distal end of an embodiment of trocar cannula assembly in a partially-assembled configuration with a balloon in a deflated state;

FIG. 26 schematically illustrates a distal end of an embodiment of trocar cannula assembly in a partially-assembled configuration with a balloon in a deflated state and a conditioning aid advanced over the balloon;

DETAILED DESCRIPTION OF THE INVENTION

Figure 1:
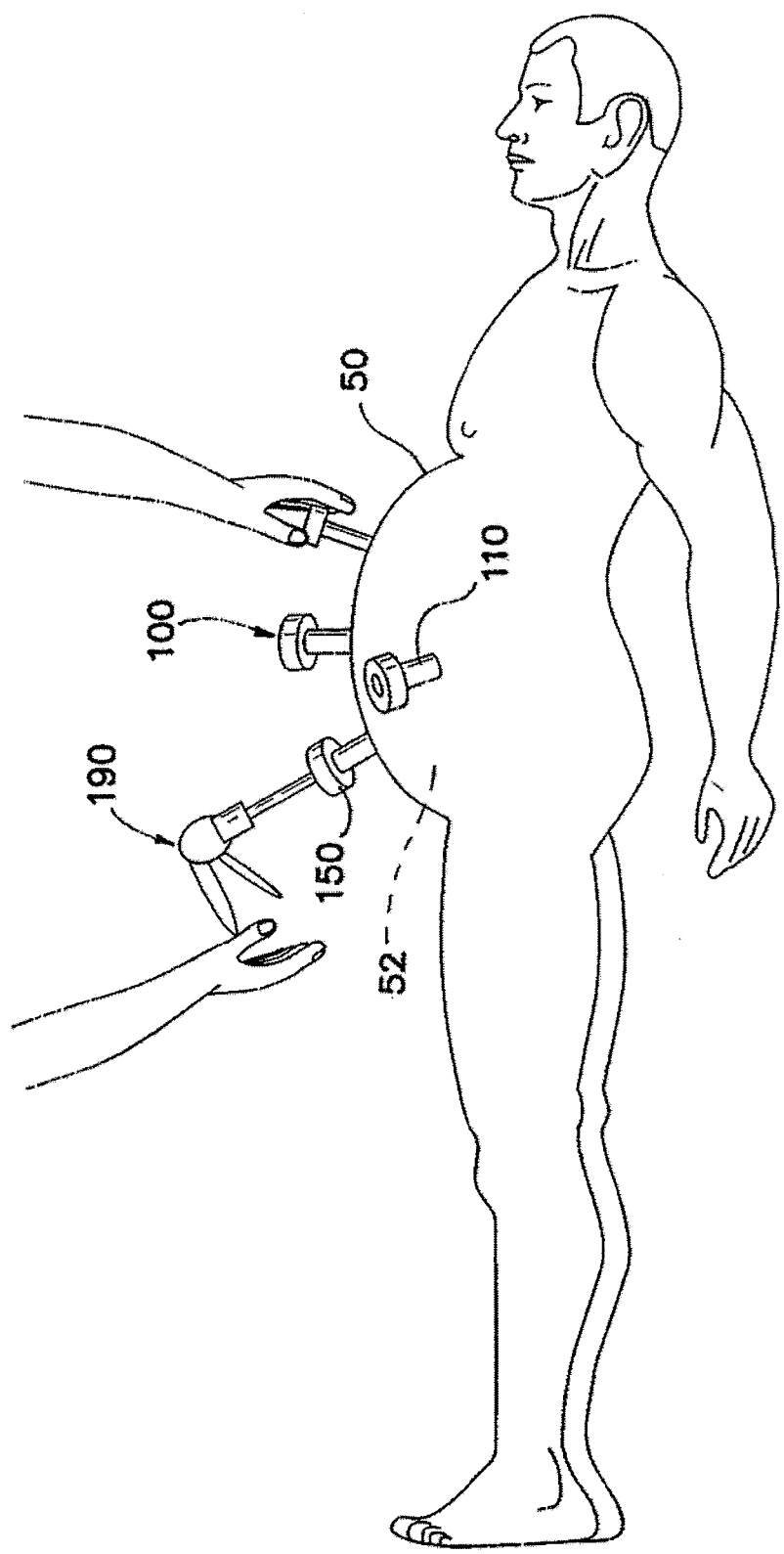
FIG. 1 illustrates a side view of a laparoscopic surgical procedure.
Figure 2:
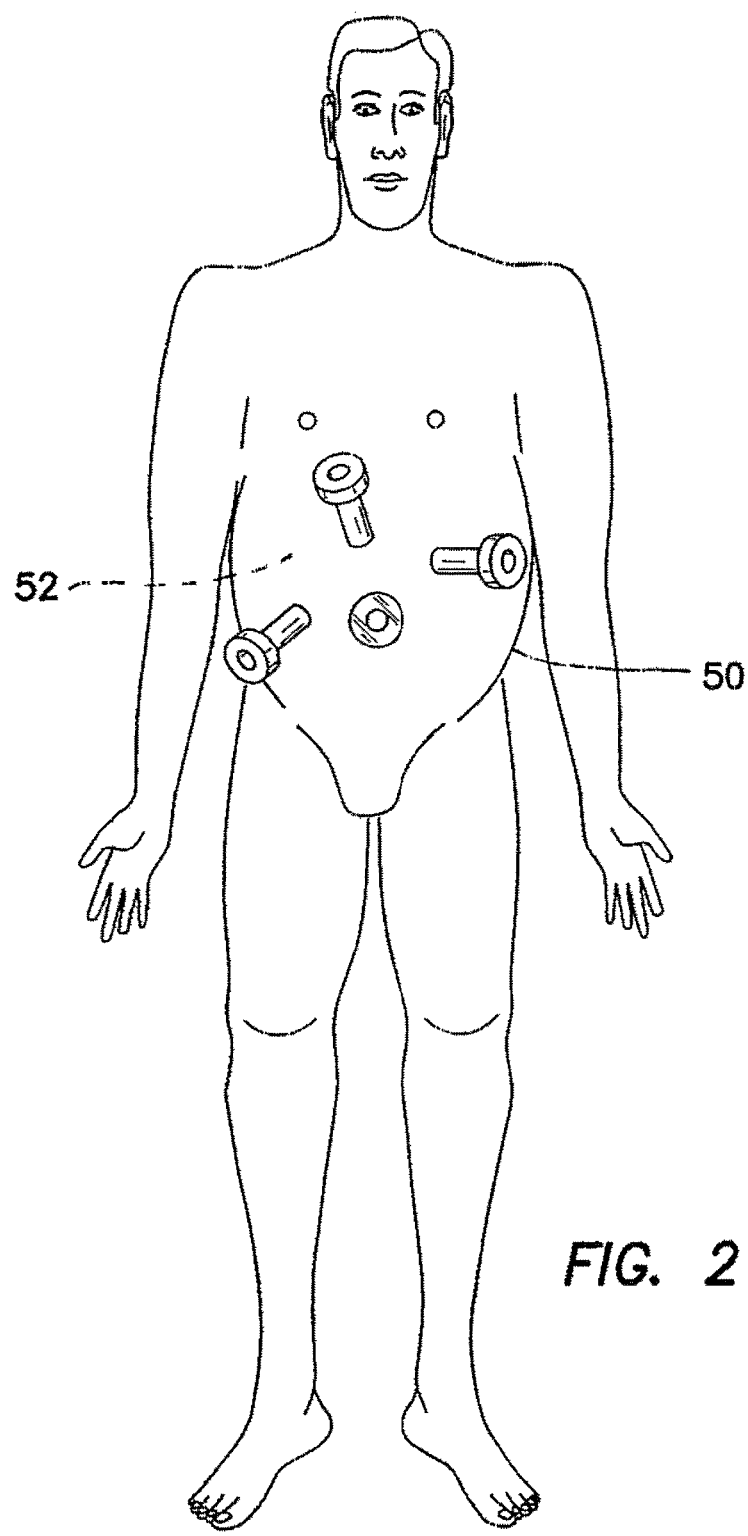
FIG. 2 illustrates a plan view of a laparoscopic surgical procedure showing the placement of trocars.
Figure 5:
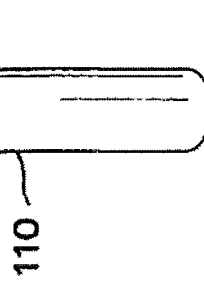
FIG. 5 illustrates a perspective view of a prior art cannula.
Figure 4:
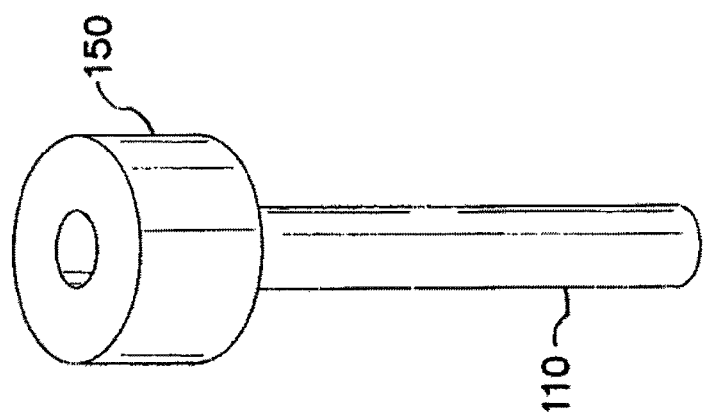
FIG. 4 illustrates a perspective view of a prior art assembled trocar without an obturator.
Figure 3:
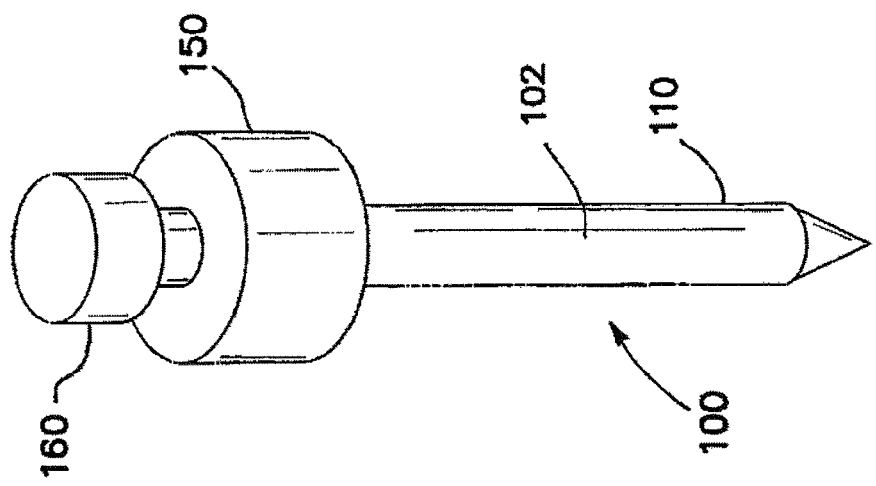
FIG. 3 illustrates a perspective view of a prior art assembled trocar and obturator.

With reference to FIGS. 1 and 2, a typical laparoscopic procedure is illustrated where a plurality of trocars 100 are placed through a body wall 50, such as an abdominal wall, and into a body cavity 52, such as an abdominal cavity. The body cavity 52 is insufflated, or inflated with gas, to distend the body wall 50 and provide a working space for the laparoscopic procedure. The trocars 100 each include a cannula 110 and a seal 150. Positive pressure is maintained within the body cavity 52 by the seal 150 associated with the cannula 110. In addition, the cannula 110 must form a gas-tight seal against adjacent tissue. If positive pressure is lost, either through the seal 150 associated with the cannula 110 or the seal between the cannula and the adjacent tissue, the procedure may be compromised.

As the body cavity 52 is inflated, the body wall 50 may be greatly distended. The access sites may tend to enlarge under the distention of the body wall 50 and compromise the positioning and sealing of the cannula 110. As stated above, the manipulation of instruments 190 used through the trocars 100 may result in movement of the cannulae 110 in either a proximal or distal direction within the access site through the body wall 50. As this occurs, some liquefaction may take place and the preferred relationship between the cannula 110 and the body tissue may be compromised.

Referring now to FIGS. 3-6, a typical assembled trocar 100 is shown having a cannula 110, a seal housing 150 and an obturator 160. The cannula 110 typically has a smooth exterior surface 102 so that it may be inserted through the body wall 50 easily. The seal housing 150 contains a seal system that prevents retrograde gas-flow. The obturator 160 is a cutting or piercing instrument that creates the pathway through the body wall 50 through which the cannula 110 follows. Surgical obturators 160 are generally sized and configured to create a defect in tissue that is appropriate for the associated cannula 110. However, the defect may have a tendency to enlarge during a surgical procedure as the trocar 100 or cannula 110 is manipulated. As an instrument 190 is urged distally and proximally, or inserted and withdrawn, the cannula 110 may move or even be inadvertently withdrawn due to the friction between the instrument 190 and the seal 150 of the trocar housing.

Figure 8:
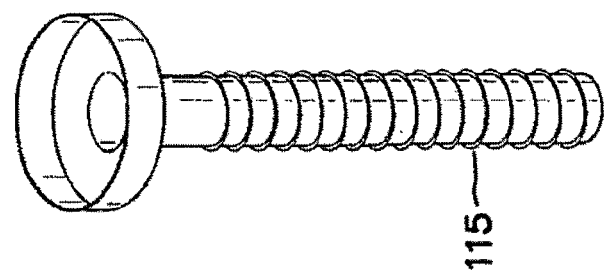
FIG. 8 illustrates a perspective view of a prior art threaded cannula.
Figure 7:
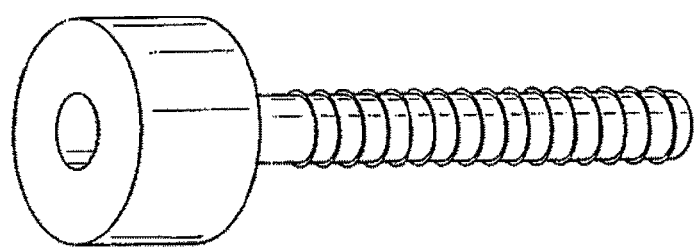
FIG. 7 illustrates a perspective view of a prior art threaded cannula and housing.
Figure 6:
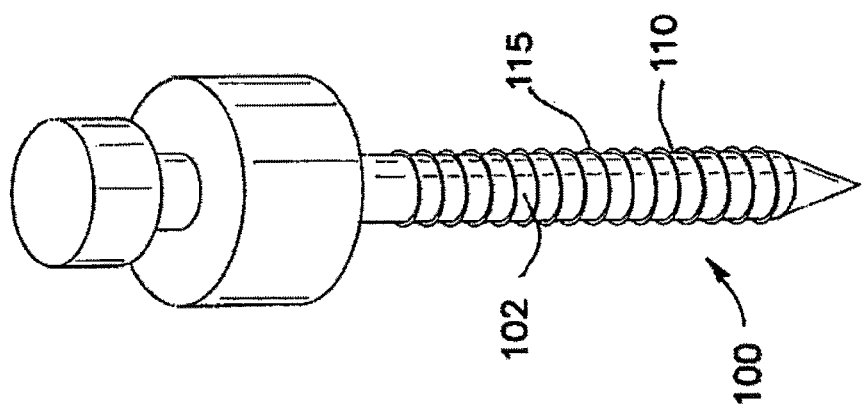
FIG. 6 illustrates a perspective view of a prior art assembled threaded trocar and obturator.
Figures 9, 10:
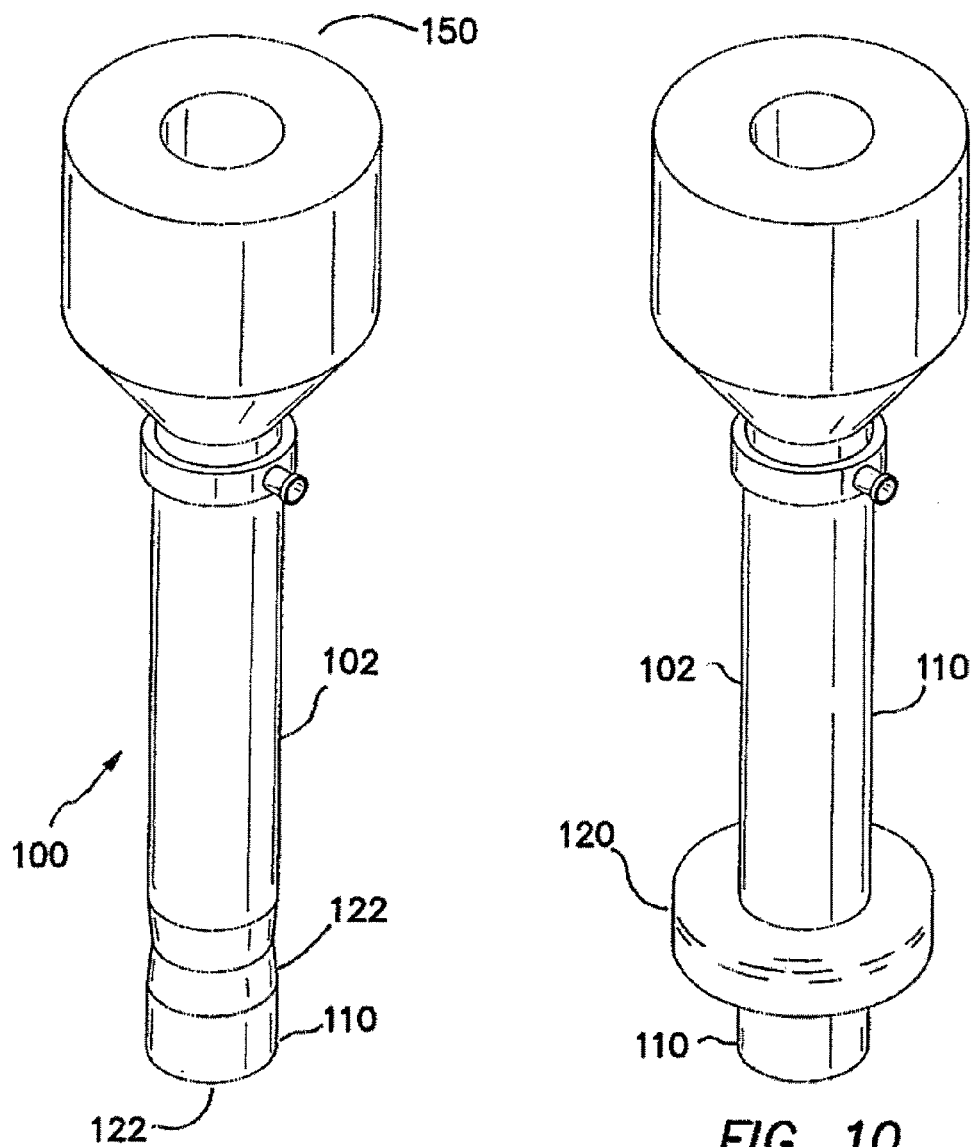
FIG. 9 illustrates a perspective view of a prior art cannula having an uninflated balloon at the distal end.
FIG. 10 illustrates a perspective view of a prior art cannula having an inflated balloon at the distal end.
Figure 11:
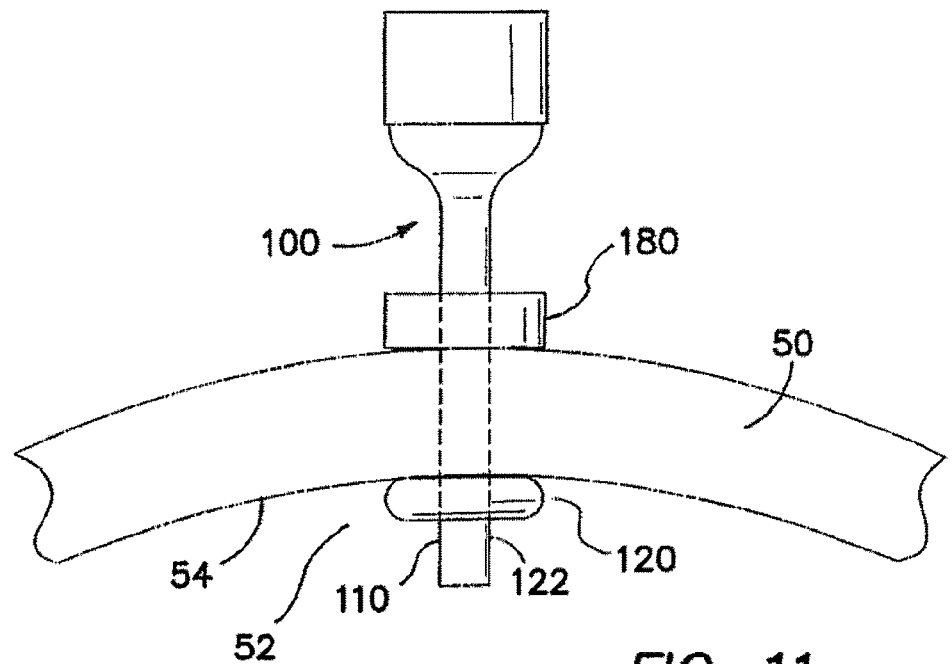
FIG. 11 illustrates a prior art trocar-cannula having a distal retention balloon placed through a body wall in a first position.
Figure 12:
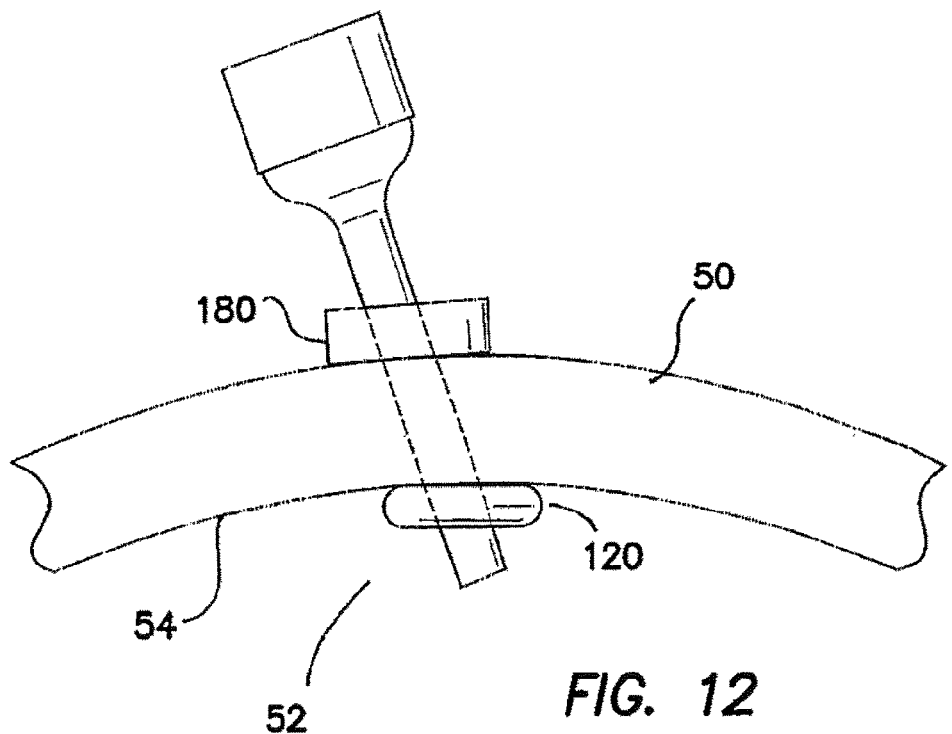
FIG. 12 illustrates a prior art trocar-cannula having a distal retention balloon placed through a body wall in a second position.

With specific reference to FIGS. 6-8, a trocar 100 or access device is shown where the outer surface 102 of the cannula 110 includes a plurality of raised features 115. These raised features 115 are sized and configured to increase resistance to proximal and distal motion as instruments 190 are maneuvered, and especially as specimens are removed, through the trocar 100. The prior art includes either sequential raised rings or a raised coarse-thread 115. While the rings or threads 115 of the prior art may stabilize the cannula 110 to some degree, they do not necessarily seal the cannula 110 against the adjacent tissue of a body wall 50. There may be gas loss associated with the use of these systems. The raised rings or threads 115 also increase the insertion force required to penetrate a body wall 50. The insertion force may be reduced in the instance of a continuous coarse thread 115 in comparison to a sequence of discrete raised rings or features as a threaded cannula 110 may actually be "screwed" into the tissue defect in accordance with the thread direction and pitch, rather than pushed through without appropriate rotation.

With reference to FIGS. 9-12, a surgical access device 100 according to prior art includes a cannula 110 having an inflatable balloon 120 associated with the distal-end portion 122 of the cannula. The balloon 120 is sized and configured to fit snugly around the cannula 110 in the uninflated condition. The balloon 120 is inflated after the cannula 110 is properly placed through the body wall 50 and into the body cavity 52. The balloon 120 is generally held against the interior surface 54 of the body wall 50 by a counter-force that is associated with a sliding counter-force member, such as a foam bolster 180. The bolster 180 is associated with the proximal portion of the cannula 110. The balloons 120 associated with the devices of the prior art are typically "thick-walled" structures constructed as part of the cannula 110. The balloon 120 is generally bonded to the distal-end portion 122 of the cannula 110 and an inflation channel or lumen is provided within the wall of the cannula 110.

Figure 13:
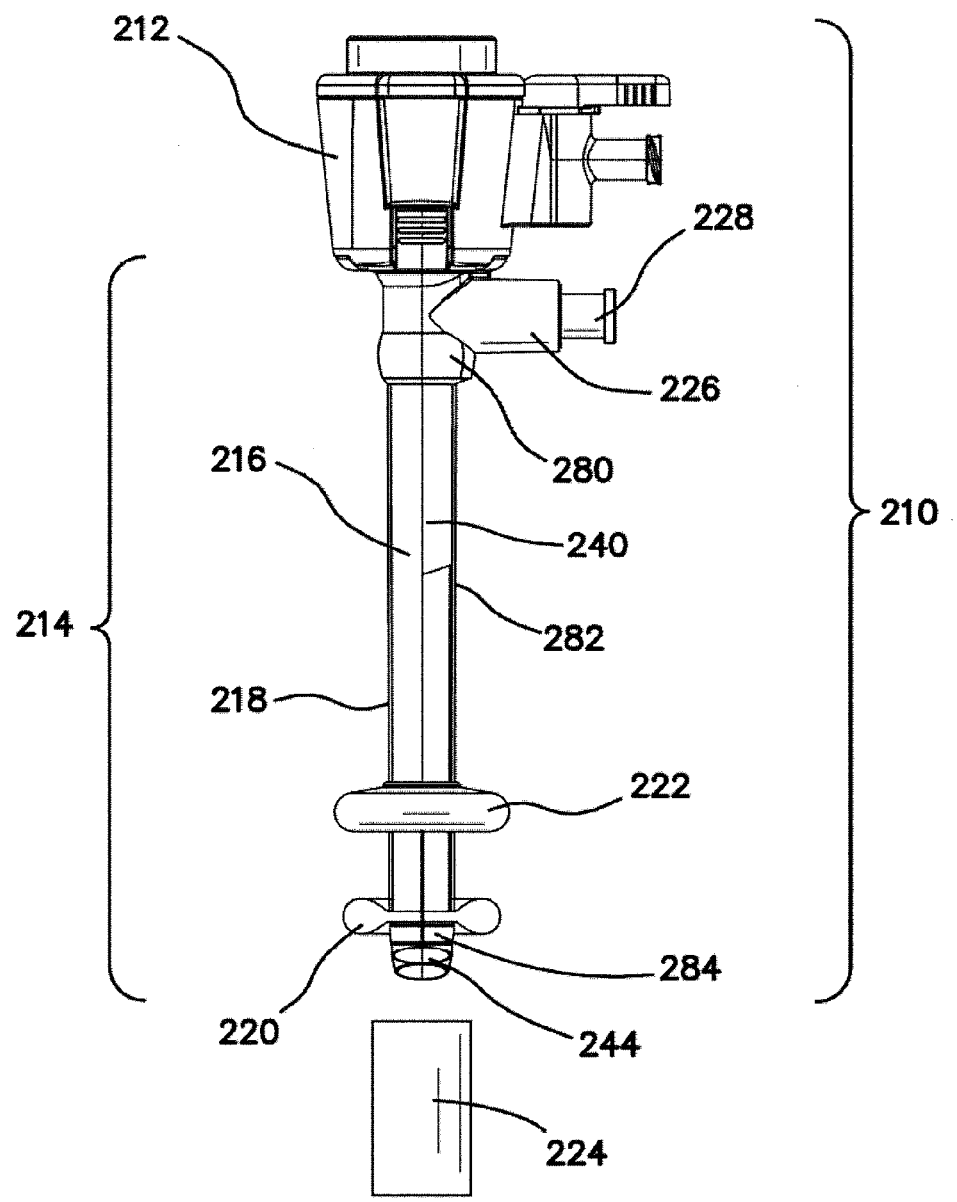
FIG. 13 illustrates a perspective view of an embodiment of trocar cannula assembly.

With reference to FIG. 13, an embodiment of trocar cannula assembly 210 having advanced fixation features is illustrated. The trocar cannula assembly 210 can include a seal housing 212 and a sleeve sub assembly 214 comprising a trocar cannula 216, a sleeve 218 including an inflatable balloon 220, a retention disc 222, and a tip protector 224 or conditioning aid. Various aspects described herein with respect to certain embodiments of trocar cannula assembly can be used in either balloon cannulae or retention cannulae.

With continued reference to FIG. 13, the seal housing 212 or valve housing can include an instrument seal and a zero seal. In some embodiments, the valve housing can be removably coupled to the cannula 216 and in one embodiment includes an inlet for supplying insufflation gas into a body cavity such as the abdominal cavity. The instrument seal and zero seal enclosed in the valve housing in various embodiments can be separate or monolithic seals. The zero seal and instrument seal can seal an instrument path through the valve housing into a lumen 236 (FIG. 14) of the cannula 216. In other embodiments, the trocar cannula 216 can have an instrument seal and a zero seal, separate or monolithic seals, positioned directly therein with no separate valve housing such that the trocar cannula with a sealed instrument channel path has a relatively short length from a proximal end to the distal end defining a low height profile.

In certain embodiments, the trocar cannula assembly 210 can be sized to receive surgical instruments such as laparoscopic surgical tools having standard sizes. For example, the trocar assembly 210 can be a "5 mm trocar cannula," sized and configured to receive surgical tools from sized up to a 5 mm surgical tool product class. In other embodiments, a trocar assembly 210 can be an "11 mm trocar cannula" or a "12 mm trocar cannula," sized and configured to receive surgical tools sized as large as an 11 mm or 12 mm surgical tool product class respectively. In some embodiments, the trocar cannula assembly 210 can be included in a kit comprising the trocar cannula assembly 210, a seal housing 212 and an obturator insertable through the seal housing 212 and the cannula assembly 210.

Figure 14:
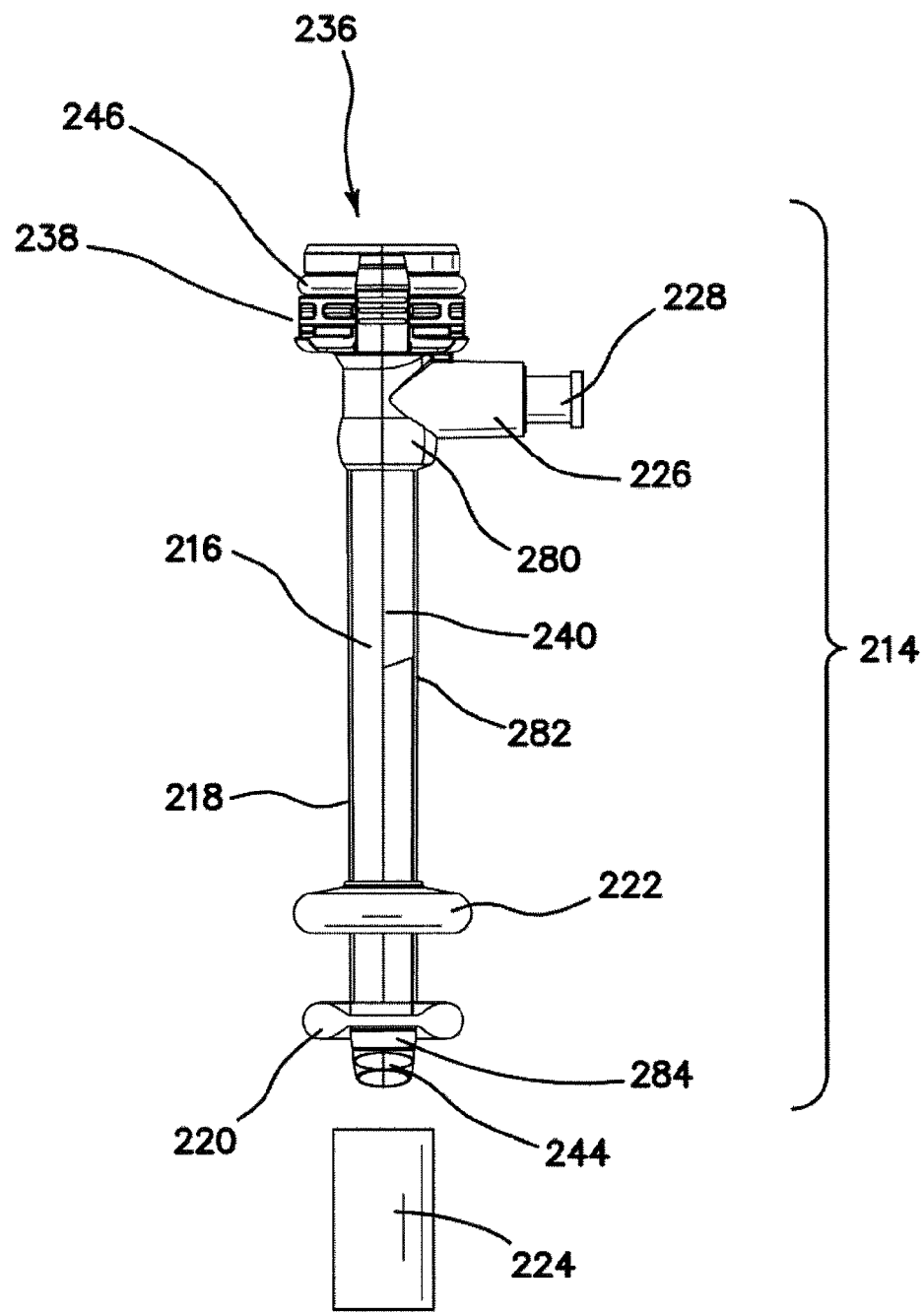
FIG. 14 illustrates a perspective view of an embodiment of sleeve subassembly of the trocar cannula assembly of FIG. 13.

With reference to FIGS. 13-14, the trocar cannula 216 can include a fluid inlet port 226. The fluid inlet port 226 is adapted to receive a source of fluid such as a syringe. The fluid can comprise air, another gas such as carbon dioxide, a gas mixture, or a liquid such as water, a saline solution, or another liquid solution. As further discussed herein, the fluid inlet port 226 is fluidly coupled to the sleeve 218 such that addition of fluid to the fluid inlet port 226 inflates the balloon 220.

In some embodiments, the fluid inlet port 226 can include a one-way valve such as a poppet valve or check valve 228. Once fluid is added to the fluid inlet port 226 through the check valve 228, the check valve 228 maintains the fluid within the sleeve 218 and balloon 220 of the trocar cannula assembly 210. The check valve 228 can be selectively opened to allow the fluid to escape or be withdrawn such as by syringe when it is desired to deflate the balloon 220.

Trocar Cannula

Figure 15:
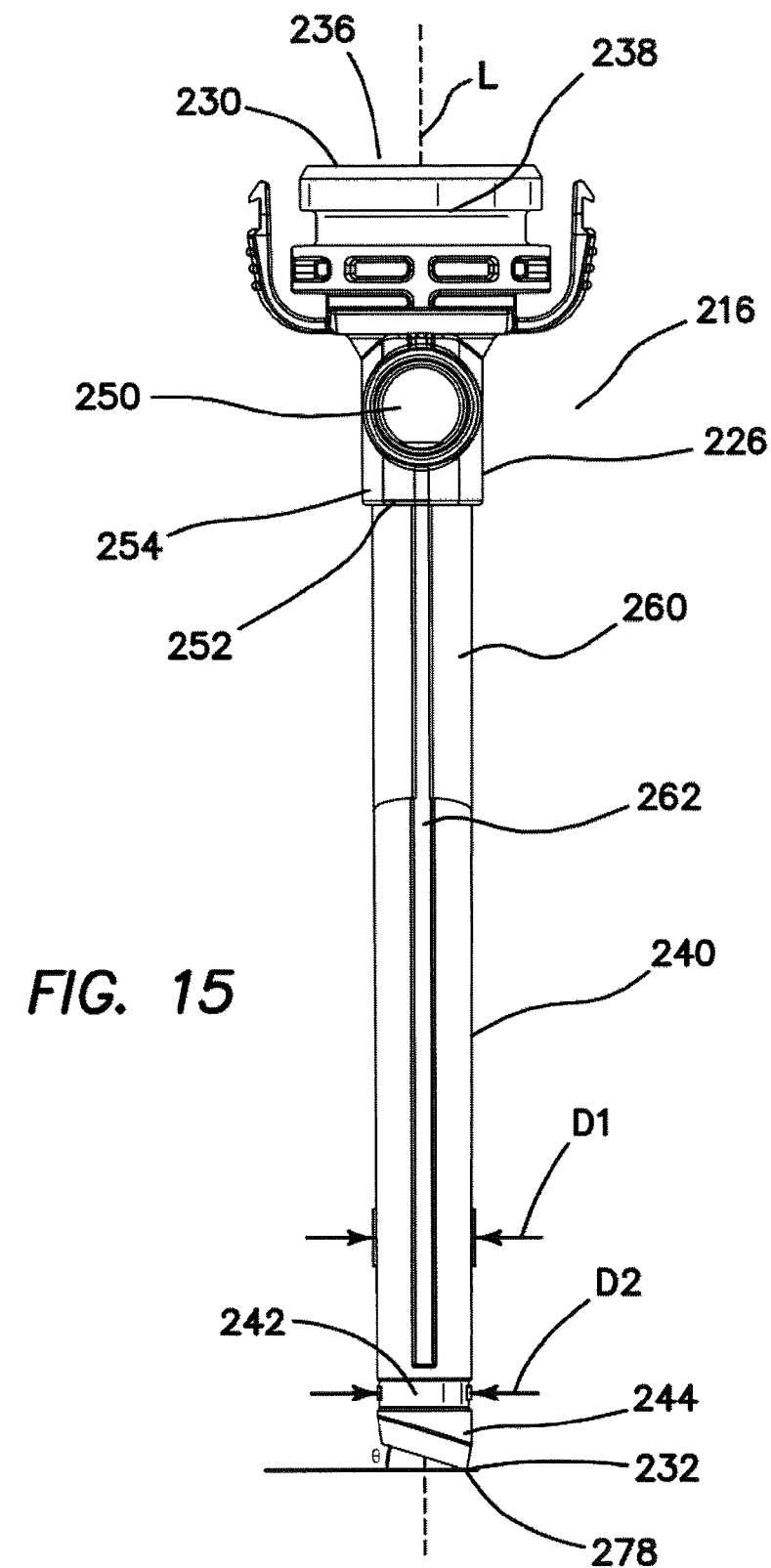
FIG. 15 illustrates a perspective view of an embodiment of cannula of the trocar cannula assembly of FIG. 13.

With reference to FIG. 15, in some embodiments, the trocar cannula 216 has a proximal end 230, a distal end 232, and a lumen 236 extending from the proximal end 230 to the distal end 232 along a longitudinal axis L. The lumen 236 is configured to receive a surgical instrument therein such as a laparoscopic surgical tool.

With continued reference to FIG. 15, in some embodiments, the trocar cannula 216 comprises a seal housing interface 238 at the proximal end 230, the fluid inlet port 226 distal the seal housing interface 238, a generally tubular cannula body 240 extending distally from the fluid inlet port 226, an annular recess such as an annular groove 242 in the cannula body 240 adjacent the distal end 232 of the cannula 216, and a distal tip 244. The seal housing interface 238 can comprise a seal such as an O-ring 246 (FIG. 14) to sealingly engage a seal housing.

In the illustrated embodiments, the fluid inlet port 226 comprises a fluid inlet 250 and a fluid dome 252. The fluid inlet 250 is configured to receive the source of inflation fluid and can include the check valve 228 positioned therein (FIG. 14).

As illustrated, the fluid dome 252 of the fluid inlet port 226 is fluidly coupled to the fluid inlet 250. In some embodiments, the fluid inlet port 226 can have a generally smooth outer surface 254. The smooth outer surface 254 can allow adhesive to flow underneath the sleeve 218 and obtain a relatively strong balloon-to-cannula bond. In some embodiments, the fluid inlet port 226 can be shaped with a curved profile such as a generally teardrop shape and the fluid dome 252 can have a curved profile to reduce the likelihood of the fluid pathway for balloon inflation/deflation can become plugged. In other embodiments, the fluid inlet port 226 can have another curved profile such as a generally cylindrical, elliptical, or oval profile. In other embodiments, the fluid inlet port 226 can have another curvilinear profile.

Cannula Body

With continued reference to FIG. 15, in some embodiments, the cannula body 240 extends distally from the fluid inlet port 226 to the distal end 232 of the cannula 216. The cannula body 240 has an exterior surface 260 and a first outer diameter D1. In some embodiments, the exterior surface 260 of the cannula body 40 can be configured to facilitate installation of the sleeve 218 thereon. For example, the exterior surface 260 of the cannula body 240 can include a relatively lightly textured surface finish to facilitate sliding advancement of the sleeve 218 over the cannula body 240.

In some embodiments, the cannula body 240 can include one or more fluid channels 262 or grooves that extend generally longitudinally from the fluid inlet port 226 towards the distal end 232 of the cannula 216. The fluid channel 262 can be formed in the exterior surface 260 of the cannula body 240 and extend a depth d into the cannula body 240. As illustrated, the fluid channel 262 is fluidly coupled to the fluid inlet port 226 and extends distally to a location adjacent the balloon 220 of the sleeve 218. (FIG. 14). The fluid channel 262 can thus work in conjunction with the balloon 220 to allow fluid passage for balloon 220 inflation and deflation. Advantageously, with the fluid channel 262 embedded in the cannula body 240, the sleeve sub-assembly 214 can have a relatively small outer diameter and low-profile. Desirably, with a relatively small diameter and low-profile, the cannula assembly 210 can have a relatively low insertion force. Similarly, the balloon 220 and fluid channel 262 geometry can reduce the incidence of the balloon 220 plugging the fluid flow path during deflation.

With continued reference to FIG. 15, the cannula body 240 can include an annular recess such as an annular groove 242 adjacent the distal end of the trocar cannula 216. In some embodiments, the annular groove 242 is formed in the cannula body 240 at an orientation generally perpendicular to the longitudinal axis L of the trocar cannula 216. In other embodiments, other orientations of the annular groove 242 can be formed. In certain embodiments, as illustrated, the annular recess comprises an annular groove 242 having a recessed surface extending a relatively short length along the longitudinal axis L of the trocar cannula 216 adjacent the distal end of the trocar cannula 216. In other embodiments, the annular recess or annular groove can include a recessed surface extending from a location adjacent the distal end proximally to a location between the proximal end or the distal end of the trocar cannula 216 or to a location adjacent the proximal end of the trocar cannula 216.

Figure 16:
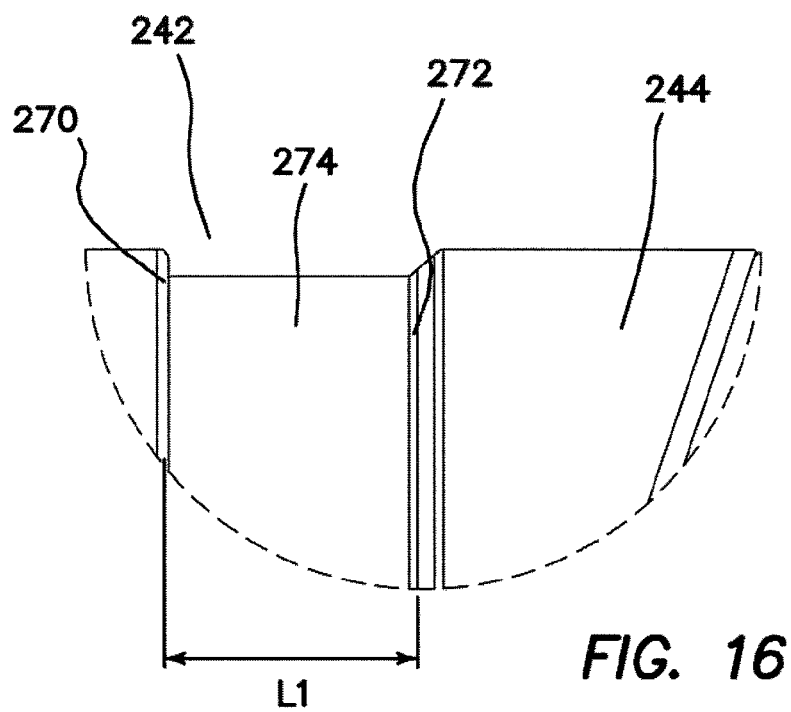
FIG. 16 illustrates a detail cut away view of a distal end of the cannula of FIG. 15.

FIG. 16 illustrates a cut away detail view of an embodiment of annular groove 242. In some embodiments, the annular groove 242 can have a proximal edge 270, a distal edge 272, and an annular interface surface 274 between the proximal edge 270 and the distal edge 272. The annular interface surface 274 can have a second outer diameter D2 smaller than the first outer diameter D1 of the cannula body 240. The proximal edge 270 can have a generally stepped edge extending between the first outer diameter D1 of the cannula body 240 and the second outer diameter D2 of the annular interface surface 274. Desirably, the stepped edge can enhance sealing performance of the sleeve 218 to the cannula body 240 to maintain fluid within the balloon 220 in an inflated configuration.

With continued reference to FIG. 16, in some embodiments, the distal edge 272 of the annular groove 242 can have a ramped edge. The ramped edge can extend at an angle transverse to the annular interface surface 274. In other embodiments, the distal edge 272 of the annular groove 242 can comprise a generally stepped edge or an edge having another geometric profile such as a radiused curvilinear edge.

With reference to FIG. 15, in some embodiments, the distal tip 244 at the distal end 232 of the cannula 216 has a distal edge 278 that extends at an angle θ relative to a plane perpendicular to the longitudinal axis L of the cannula 216. The angle θ can be between about 5 degrees and about 45 degrees. In some embodiments, of cannula assembly 210 having a 5 mm size, the distal edge 278 of the distal tip 244 can be angled at approximately 17 degrees relative to the plane perpendicular to the longitudinal axis L. In embodiments of cannula assembly 210 having other sizes, for example 11 mm and 12 mm cannulae, the angle can be slightly different to match the correlated cannulae 216. For example, in some embodiments of 11 mm cannula assembly, the angle θ can be approximately 20 degrees, and in some embodiments of 12 mm cannula assembly, the angle θ can be approximately 12 degrees. In other embodiments of cannula assembly 210 other angles can be used.

Advantageously, the angled distal tip 244 can greatly reduce the force required to insert the cannula assembly 210 through a body wall such as the patient's abdominal wall as compared with a distal tip having a straight tip with a distal edge perpendicular to the longitudinal axis of the cannula. Balloon trocars having straight tips have primarily been introduced through body walls into surgical sites through relatively large incisions using a cut-down technique. Desirably, the angled distal tip 244 can facilitate the use of a fixation cannula in surgical procedures including various cannula insertion techniques with various incision lengths. For example, a fixation trocar having an angled distal tip can be inserted with a relatively low insertion force with insertion techniques including insertion techniques with bladed, non-bladed optical, or insufflation obturators.

In some embodiments, the cannula body 240 can be formed of a polycarbonate material. Desirably, the hardness and relative rigidity of the material allows the cannula 216 to serve as a supporting tube to install the flexible sleeve 218 and balloon 220 and a port to insert obturators or other medical instruments. In other embodiments, the cannula body 240 can comprise other materials, such as, for example polyester materials.

Sleeve

In certain embodiments, a sleeve extends from adjacent the proximal end of the trocar cannula to adjacent the distal end of the trocar cannula. The sleeve has a proximal end and a distal end with an inflatable segment adjacent the distal end. The sleeve can be coupled to the trocar cannula at the proximal end of the sleeve and the distal end of the sleeve.

The sleeve can be coupled to the trocar cannula by a technique that creates a relatively low diametric profile at the coupling, has desirable sealing performance, and can be efficiently manufactured. For example, in some embodiments, the trocar cannula can have a substantially smooth continuous outer surface, and the sleeve can be coupled to the smooth surface by application of an adhesive to form a chemical bond. In other embodiments, the sleeve can be coupled to the trocar cannula by heat welding or UV welding to create a fused coupled region. In some embodiments, as further discussed with respect to FIGS. 17-19, the sleeve can be coupled to the trocar cannula at a non-continuous region of the outer surface, such as, for example one or more annular grooves formed therein. In some embodiments, different coupling techniques can be used at the proximal end of the sleeve than are used at the distal end, while in other embodiments, substantially similar coupling techniques can be used at the proximal end and the distal end of the sleeve.

Figure 18:
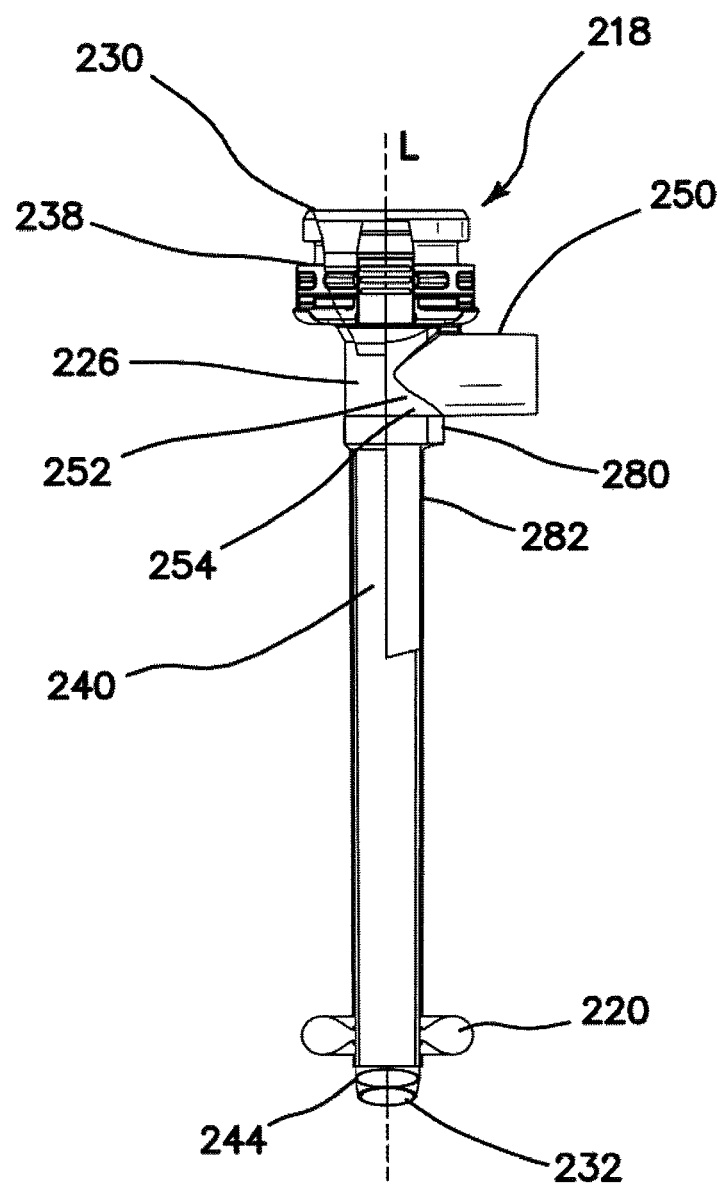
FIG. 18 illustrates a partial cross-sectional view of an embodiment of trocar cannula assembly in a partially-assembled configuration.

With reference to FIG. 18, an embodiment of sleeve 218 and cannula assembly 210 is illustrated. In the illustrated embodiment, the sleeve 218 comprises a proximal interface section 280 or coupler at the proximal end 281, an elongate tubular body 282 extending distally from the coupler, a balloon 220 positioned distal the elongate tubular body 282, and a bonding segment 284 distal the balloon.

In some embodiments, the sleeve 218 can be monolithically unitarily formed, such as by stretch blow molding. Advantageously, the stretch-blow molding process allows for a high degree of control of the balloon material, thickness and shape.

The sleeve 218 can comprise a polyolefin material such as one commonly used as heat shrink tubing. In certain embodiments, a Sumitomo A2 clear polyolefin tubing can be used. Advantageously, a sleeve 218 comprising a polyolefin material, is latex free, non-porous, and non-fragmenting, unlike latex or silicone rubber materials. Desirably, the polyolefin tubing material can be soft, flexible, and can include a high degree of cross-linking such that it has a relatively high strength for a given material thickness compared to other tested materials. In embodiments of cannula assembly 210 having a polyolefin sleeve 218, despite having an incredibly thin balloon section, the balloon 220 can typically be over-inflated with an average of 5 times of a designed inflation pressure without rupturing. Also, the softness and flexibility of the polyolefin material improves the feel of the device for the user while also reducing the insertion force. In other embodiments the sleeve can comprise other materials such as a silicone material, cilran, polyisoprene, a polyurethane material, a polyurethane blend, TYGON®, VITON®, SANTOPRENE®, MYLAR®, or another suitable polymeric material.

In the illustrated embodiment, the cannula assembly includes one balloon 220 positioned at a distal location on the cannula 216. It is contemplated that in various other embodiments, additional balloons can be incorporated to account for variations in a patient's abdominal wall thickness and anatomy. Also, balloons at different locations may use different material. The balloon may be distensible or non-distensible or a combination of both. The balloon 220 in one embodiment is doughnut shaped or in one aspect disc-like. The size and/or location of the balloon 220 can vary to vary the desired retention of the trocar cannula 216 with the patient's body.

With continued reference to FIG. 18, the coupler 280 is sized and configured to engage the cannula 216. For example, in the illustrated embodiment, the coupler 280 has a curved profile in an eccentric or generally teardrop shape to match the teardrop shape of the fluid dome 252 of the cannula 216. Advantageously, this matching profile can allow a tight fit when the sleeve 218 is installed on to the cannula 216, reducing the potential for leakage therebetween.

In some embodiments, an outer surface of the coupler at the proximal end 281 is textured. The rough surface facilitates the bonding of adhesives to the sleeve 218, preventing the sleeve 218 from being separated from the cannula 216 when the balloon 220 is fully inflated. For example, a roughened or textured surface can create a plurality of relatively small channels which enhance flow of a chemical adhesive though a wicking or capillary action process to create a strong adhesive bond between the sleeve 218 and the cannula 216. Desirably, a textured or roughened surface at the coupler can allow the sleeve 218 to comprise a material that can be otherwise difficult to bond with adhesives.

With continued reference to FIG. 18, the elongate tubular body 282 or shaft of the sleeve 218 extends distally from the coupler 280. The shaft is uniform and thin-walled, but thick enough to withstand sliding movement of a retention disc 222 or other bolster.

Figure 19:
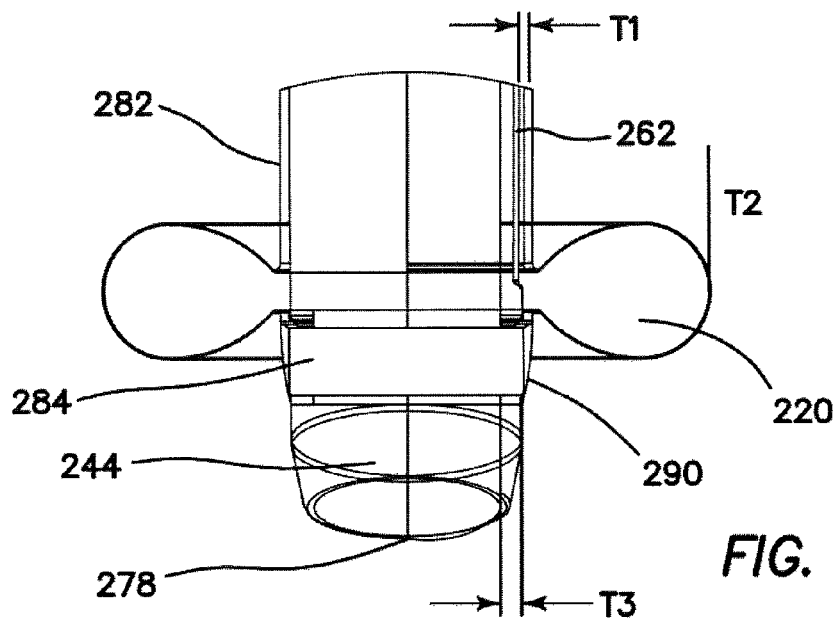
FIG. 19 illustrates a partial cross-sectional view of the distal end of the trocar cannula assembly of FIG. 13.

FIG. 19 illustrates a distal end of the cannula assembly 210 with the sleeve 218 positioned on the cannula 216. Advantageously, a sleeve 218 formed by a stretch blow molding process can allow for increased control of the thickness t1 of the elongate tubular body 282 to minimize an outer diameter of the trocar cannula assembly 210 resulting in a smaller incision size for the patient. In some embodiments, the elongate tubular body 282 can have a thickness t1 of approximately 0.008 inches to approximately 0.012 inches.

With continued reference to FIG. 19, as illustrated, the sleeve 218 comprises a non-distensible inflatable balloon 220 distal of the elongate tubular body 282. The balloon 220 can have a thickness t2 that is smaller than the thickness t1 of the elongate tubular body 282. Advantageously, stretch blow molding a polyolefin material to form the balloon 220 can provide a high strength material with a relatively low thickness. In some embodiments, the balloon can have a thickness between about 0.0005 inches and 0.002 inches. In certain embodiments, the balloon can have a thickness of approximately 0.0015 inch.

Advantageously, abrupt thickness transitions at the balloon/shaft interfaces can be significantly reduced or eliminated through the stretch blow molding process. Desirably, the relatively high degree of control in the balloon thickness of the stretch blow molding process can also contribute to a minimized outer diameter adjacent the distal end of the cannula assembly, resulting in a reduction in insertion force.

Figure 17:
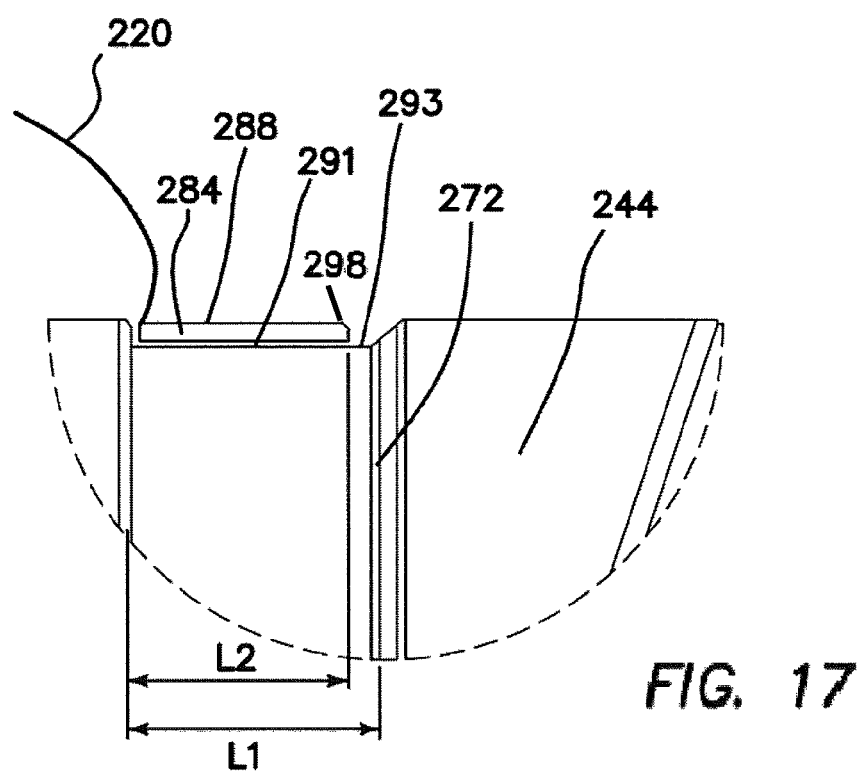
FIG. 17 illustrates a detail cut away view of the trocar cannula assembly of FIG. 13.

With reference to FIG. 17, the sleeve 218 can have a chamfered leading edge 298 at the distal end thereof. Desirably, the angle of the chamfered leading edge 298 with respect to a longitudinal axis of the bonding segment 284 can be chosen to provide a smooth transition between the distal end of the cannula and the distal end of the sleeve. Such a smooth transition can contribute to a reduction in insertion force for the trocar cannula assembly as compared with a trocar cannula assembly having a generally squared corner at the distal end. In some embodiments, the angle of the chamfered leading edge 298 can be between approximately 50 degrees and approximately 65 degrees relative to the longitudinal axis of the bonding segment 284.

FIGS. 17 and 19 illustrate a cut-away detail view of the distal end of the cannula assembly 210 with the sleeve 218 positioned on the cannula 216. In some embodiments, the outer surface 288 of the bonding segment 284 at the distal end 283 of the sleeve 218 is textured, providing a rough bonding surface to assist in the bonding of adhesives to the sleeve 218 by retaining adhesive and to promote flow of the adhesives between the sleeve and the cannula by wicking of adhesive through a capillary action process. In some embodiments, the annular interface surface 274 of the annular groove 242 is textured such as with small pits, grooves, or a roughened surface to assist in the bonding of the sleeve to the cannula. In some embodiments, a combination of cyanoacrylate instant adhesive and UV cure adhesive can be used for the sleeve-cannula bond coupling the bonding segment 284 to the annular groove 242. In other embodiments, other adhesives, such as only a cyanoacrylate adhesive or only a UV cure adhesive, or another type of adhesive can be used. Desirably, the adhesive can be applied substantially within the annular groove 242 such that the distal end 232 of the cannula 216 can have a smooth low profile transition between the sleeve 218 and the cannula 216. Advantageously, the low profile transition between the sleeve 218 and the cannula 216 can reduce the insertion force required to position the cannula assembly 210 in a surgical site.

In some embodiments, the low profile transition can be further enhanced by disposition of an adhesive 290 predominantly within the annular groove 242 of the cannula body 240. The bonding segment 284 of the sleeve 218 and the annular groove 242 of the cannula 216 can be sized and configured to facilitate the disposition of the adhesive 290 predominantly within the annular groove 242. For example, in some embodiments, the annular surface of the annular groove has a first length l1 along the longitudinal axis of the cannula, the bonding segment has a second length l2 along the longitudinal axis of the cannula, and the second length is smaller than the first length. Thus, in some embodiments, the annular interface surface 274 of the annular groove 242 can comprise an engagement segment 291 and an exposed segment 293. The engagement segment 291 can be defined by the second length l2 and engaged by the bonding segment 284. The exposed segment 293 can be defined by a difference between the first length l1 and the second length l2. The exposed segment 293 can desirably be sized to provide a sufficient surface for disposition of a bead of adhesive to maintain the bonding segment 284 of the sleeve 218 with respect to the annular groove 242. Thus, in some embodiments, an adhesive 290 can be at least partially applied to the exposed segment 293 of the annular interface surface 274 to couple the bonding segment 284 to the annular groove 242.

In some embodiments the sleeve 218 can be adhesively bonded to the cannula 216 at the proximal interface surface 280 or coupler with a combination of cyanoacrylate instant adhesive and UV cure adhesive similar to the adhesive bonding of the bonding segment 284 to the annular groove 242. In other embodiments, other adhesives, such as only a cyanoacrylate adhesive or only a UV cure adhesive, or another type of adhesive can be used.

Retention Disc

Figure 21:
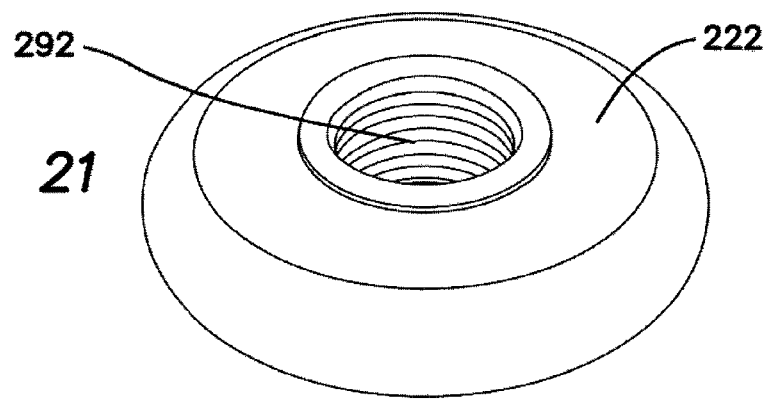
FIG. 21 illustrates a perspective view of a retention disk of the trocar cannula assembly of FIG. 13.
Figure 22:
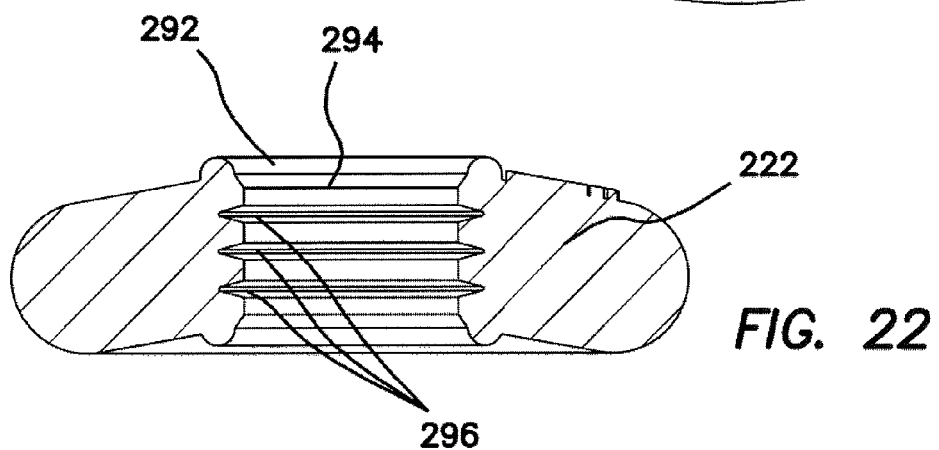
FIG. 22 illustrates a cross-sectional view of the retention disk of FIG. 21.

FIGS. 21 and 22 illustrate a retention disc 222 for positioning on the cannula assembly 210. In some embodiments, the cannula assembly 210 includes a proximal fixation member such as a retention disc 222 positioned proximal the balloon 220 around the elongate tubular body 282 of the sleeve 218. After the trocar cannula assembly 210 is inserted through a body wall at a surgical site, the balloon 220 can be inflated to maintain the position of the trocar cannula assembly 210 in the surgical site, and the proximal fixation member or retention disc 222 can prevent the trocar cannula 216 from advancing further into the surgical site.

As illustrated in FIG. 22, the retention disc 222 can comprise a generally circular disc with a center hole 292 defining a passage 294 through the retention disc 222. The passage 294 of the center hole 292 can have a ribbed profile on an inner diameter. The ribbed profile can include a plurality of annular grooves 296. The ribbed profile can frictionally engage an outer surface of the elongate tubular body 282 of the sleeve 218 such that the retention disc 222 is manually slidable along the sleeve 218 but tends to remain in a selected position.

In some embodiments, the retention disc 222 can be formed of an elastomeric polymer material such as a KRATON® material. A retention disc 222 formed of a KRATON® material can provide a desired level of frictional engagement with the outer surface of the sleeve 218 and present an ergonomically pleasing soft, flexible feel to a user of the trocar cannula. Advantageously, the round corners and soft material of the retention disc 222 provide an atraumatic means to hold the trocar in place. In some embodiments, the retention disc 222 can be formed by an injection molding process. Advantageously, embodiments of a trocar cannula having a single molded retention disc 222 can have manufacturing and assembly efficiencies and facilitate ease of use relative to a clamp mechanism having multiple assembled components.

In some embodiments, the trocar cannula assembly 210 can be configured to resist movement of the retention disc 222 proximally along the cannula body 240 to prevent the trocar cannula 216 from advancing further into the surgical site. For example, an exterior surface 260 of the cannula body 240 can have a slight taper such that it has a smaller outer diameter at the distal end relative to the outer diameter at the proximal end of the cannula body. Thus, a friction force generated by the frictional engagement between the retention disc 222 and the sleeve 218 can increase as the retention disc 222 is slid proximally along the trocar cannula 216. The retention disc 222 can be used to fixate the trocar cannula 216 relative to a body wall. The tight fit, ribbed profile, and tapered cannula 216 prevent the retention disc 222 from advancing along the cannula body 240 when an instrument is inserted into the cannula 216.

In some embodiments, a retention disc 222 comprising an elastomeric polymer material can exhibit creep when stored under tension. Advantageously, where the exterior surface 260 of the cannula body 240 includes a slight taper, before use the retention disc 222 can be positioned adjacent the distal end having a relatively small outer diameter when not in use to reduce the incidence of creep in the retention disc 222. During use, the retention disk 222 is advanced proximally up the shaft of the cannula 216 to an area of larger cannula diameter, allowing placement and fixation of the disc 222. Additionally, such a tapered cannula body 240 can have further advantages in manufacturability of the cannula body 240. For example, such a tapered profile can facilitate release of the cannula body 240 from a mold in embodiments where the cannula body 240 is formed with an injection molding process.

In other embodiments, the cannula assembly 210 can comprise a bolster 222' such as a generally cylindrical or conical stability member with a clamp mechanism. For example, in some embodiments the cannula assembly 210 can include a stability assembly including one of the various clamp mechanisms described in U.S. Pat. No. 8,162,893, to Okihisa et al., entitled "TROCAR STABILITY ASSEMBLY," which is incorporated herein by reference in its entirety.

Conditioning Aid and Balloon Folding

Figure 20:
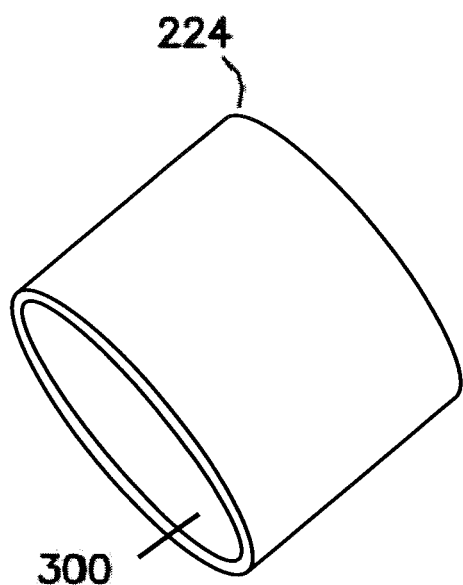
FIG. 20 illustrates a perspective view of a conditioning aid of the trocar cannula assembly of FIG. 13.

With reference to FIG. 20, in some embodiments, a trocar assembly 210 can include a conditioning aid 224 to constrict the balloon 220 relative to the body 240 and to protect the balloon 220 during shipping. Moreover, the required insertion force can be observed to vary proportionally with an overall outer diameter of the trocar cannula assembly 210 at the balloon 220. Thus, before use, it can be desirable to reduce insertion force by folding the balloon 220 into an insertion configuration having a low diameter and relatively smooth transition from the distal tip 244 of the cannula 216 to the balloon 222.

A non-elastic or non-distensible balloon 220 in a deflated or insertion configuration does not automatically conform to the exterior surface 260 of the cannula body 240. In some embodiments, the material can have a tendency to wrinkle, form folds and/or creases and may project at various points away from the exterior surface 260 of the cannula body 240. The irregularities that the un-inflated balloon may possess, can present resistance during insertion of the un-inflated retention balloon 220 through a body wall. Folding the balloon 220 into the insertion condition can reduce the force required for insertion. In some embodiments, in the insertion configuration the balloon 220 is folded along the cannula body 240 towards the proximal end 230 of the cannula 216. Folding the balloon 220 towards the proximal end 230 can result in one or more folds in the balloon 220 in the insertion configuration. For example, in some embodiments, the balloon 220 can be folded proximally in a single step and in other embodiments, the balloon 220 can be initially folded distally in a first fold and subsequently folded proximally in a second fold. By folding the balloon 220 against the trocar placement direction, it helps reduce the insertion force and lower the balloon diametric profile. The conditioning aid 224 can maintain the balloon 220 in the insertion configuration until it is removed from the trocar cannula assembly 210 for insertion to a surgical site. Moreover, the conditioning aid 224 can protect the balloon 220 and/or distal tip 244 of the cannula assembly 210 from damage during shipping or prior to operational use.

Advantageously, a trocar cannula system can achieve have a reduced diameter and relatively low insertion force if the conditioning aid 224 is advanced over the balloon 220 to constrict the balloon 220 relative to the body 240 when the balloon is in a formable state. For example, as further discussed below with respect to FIGS. 29-30, with a stretch blow molded balloon, the conditioning aid 224 can be advanced over the balloon 220 when the balloon retains residual heat. The duration of the formable state can vary based on the material used and the thickness of the balloon 220. Accordingly, it can be desirable to monitor the temperature of the balloon material and/or the elapsed time from the formation of the balloon to ensure application of the conditioning aid 224 while the balloon 220 is in the formable state. The conditioning aid 224 can thus constrict the formed balloon 220 against the cannula as it cools. Advantageously, constricting the balloon 220 against the cannula body while the balloon 220 is in a formable state can achieve a lower outer diameter relative to folding an equivalent previously-formed balloon against the cannula body. Moreover, further significant reductions in insertion force can be observed if the balloon 220 is folded in a two-step process (with an initial distal tuck or fold followed by a second distal fold) while the balloon retains residual heat and before positioning of the conditioning aid 224 on the cannula body.

FIG. 20 illustrates a conditioning aid 224 comprising a hollow tubular segment. In the illustrated embodiment, the conditioning aid 224 comprises a section of tubing having an interior surface 300 with an inner diameter. The inner diameter of the interior surface 300 is sized to provide a snug fit over the folded balloon 220 of the trocar cannula assembly. The illustrated tubular segment conditioning aid 224 is a relatively simple construction which can desirably provide certain manufacturing and assembly efficiencies. In other embodiments, conditioning aids can take on many forms such as, for example, shrink tubing, a cap, a cone or a coil of appropriate inside diameter. In certain embodiments. the conditioning aid can be made from a variety of materials, including, for example, thermoplastics, thermosets, metals and glass. In some embodiments. the conditioning aid can be generally conical or can include a tapered interior surface to facilitate removal prior to use. Desirably, the conditioning aid can have a smooth interior surface to optimize conditioning and prevent damage to the balloon.

In one embodiment, It can be desired that the conditioning aid 224 is configured to prevent proximal movement of the conditioning aid 224 past the balloon 220. In some embodiments, the conditioning aid 224 is shaped to have a somewhat smaller diameter at a distal end than at a proximal end to prevent the conditioning aid 224 from moving proximally and past the balloon 220 to maintain the conditioning aid 224 on the balloon 220. In other embodiments, the conditioning aid 224 may have detents or projections that prevent the conditioning aid 224 from moving proximally. In some embodiments, the cannula assembly 210 can further comprise a spacer between the retention disk 222 or bolster 222' and the conditioning aid 224 to prevent the conditioning aid 224 from moving proximally past the balloon 220. The retention disk 222 or bolster 222' in one embodiment is positioned near the balloon 220 or the conditioning aid 224 is sufficiently long to contact the retention disk 222 or bolster 222' to prevent the conditioning aid 224 from moving proximally past the balloon 220. Preventing the conditioning aid 224 from moving proximally past the balloon 220 prevents the conditioning aid 224 from losing contact with the balloon 220 losing pressure and protection of the balloon 220 and tip 244.

Method of Manufacture

FIGS. 23-30 illustrate various embodiments of methods for manufacture of trocars described herein. Embodiments of cannula assembly 210 discussed herein can include a preformed sleeve 218. In some embodiments, the cannula 216 can be formed from a suitable material, such as a polycarbonate or polyester material, with an injection molding process.

Figure 29:
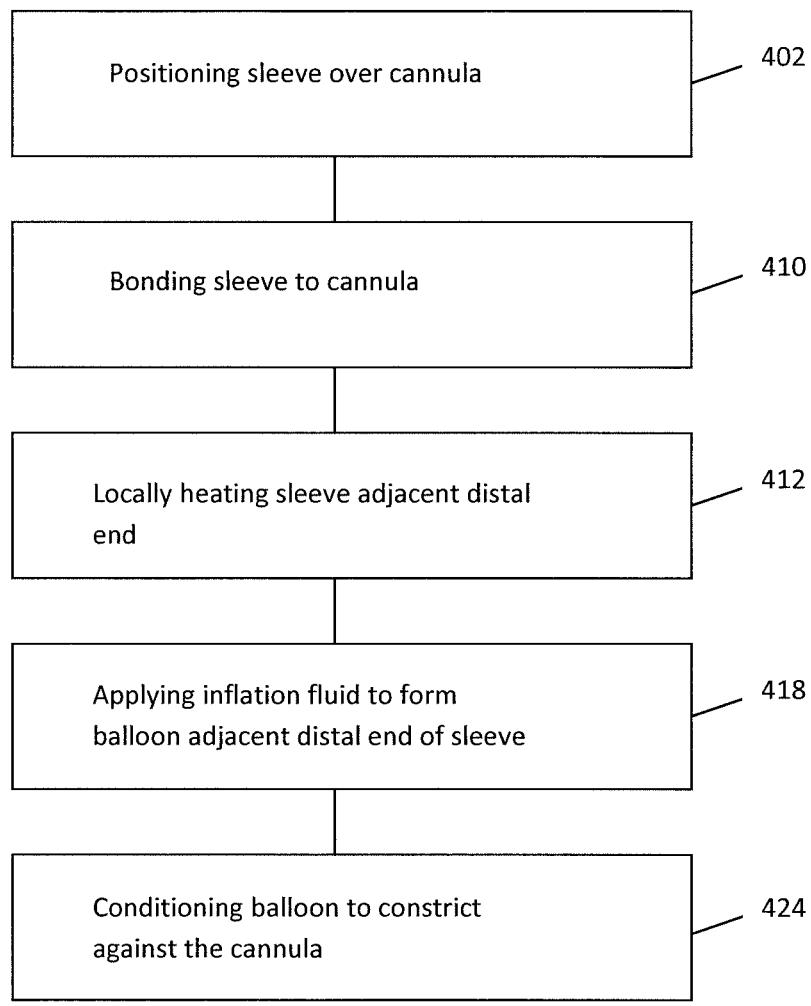
FIG. 29 illustrates an embodiment of a method for manufacturing a trocar cannula assembly.

With reference to FIG. 29, a method of making a cannula assembly 210 is illustrated. In some embodiments, a roll of polyolefin heat-shrink tubing is cut into sections or blanks then heated to shrink the tubing down to an installation size slightly larger than the cannula 216. The sleeve 218 can then be positioned 402 over the cannula 216. Once the slightly oversized sleeve 218 is installed on the cannula 216, the sleeve 218 can be heated 416 to shrink onto the exterior surface 260 of the cannula body 240. For example, the elongate tubular body 282 of the sleeve can be formed line-to-line for installation and then heated slightly to shrink down onto the exterior surface 260 of the cannula body 240. The sleeve 218 is positioned 402 over the cannula 216. The sleeve 218 can be advanced until the proximal interface section 280 of the sleeve 218 is positioned about a fluid inlet port 226 of the cannula 216 and the bonding segment 284 of the sleeve 218 is positioned 412 in the annular groove 242.

With reference to FIG. 29, in some embodiments, once the sleeve has been positioned 402 on the cannula 216, the sleeve 218 can be trimmed on the proximal end 281 and cut at the distal end 283 to form or create a chamfered leading edge 298.

With reference to FIG. 29, once the preformed sleeve 218 has been advanced over the cannula 216 and the bonding segment 284 of the sleeve 218 is positioned within the annular groove 242 of the cannula 216, the sleeve 218 can be coupled or bonded 410 to the cannula 216. For example, in some embodiments, the proximal end 281 of the sleeve 218 and the distal end 283 of the sleeve 218 are each bonded 410 to the cannula 216. In some embodiments, the proximal interface section 280 of the sleeve 218 is adhered to a location adjacent the proximal end 230 of the cannula 216 and the bonding segment 284 is adhered to the annular groove 242. For example, one or more of a cyanoacrylate adhesive and a UV cure bonding adhesive can be used to couple the sleeve 218 to the cannula 216.

The retention disc 222 can be positioned proximally of the balloon 220 around an outer surface of the sleeve 218. When installing the retention disc 222 on to the sleeve sub assembly 214, a fixture can be used to slightly expand the disc 222 to install over the balloon 220 and to avoid any possible balloon 220 damage.

With continued reference to FIG. 29, once the sleeve 218 has been positioned 402 on and bonded 410 to the cannula, the subassembly is then locally heated 412 at the distal end proximal to the bonding site. The amount of material that is heated goes directly into forming the balloon and determines the wall thickness of the balloon. Excellent control of wall thickness can be achieved by selecting the appropriate width of the heating elements that deliver heat to the section of tubing to be formed into the balloon. For example, heating elements that are 0.200" wide consistently produce balloons with a perimeter wall thickness of 0.0015" (+/−0.0005"). In other embodiments, different sized heating elements can locally heat the distal end of the sleeve 218 to form balloons having different thicknesses.

Figure 23:
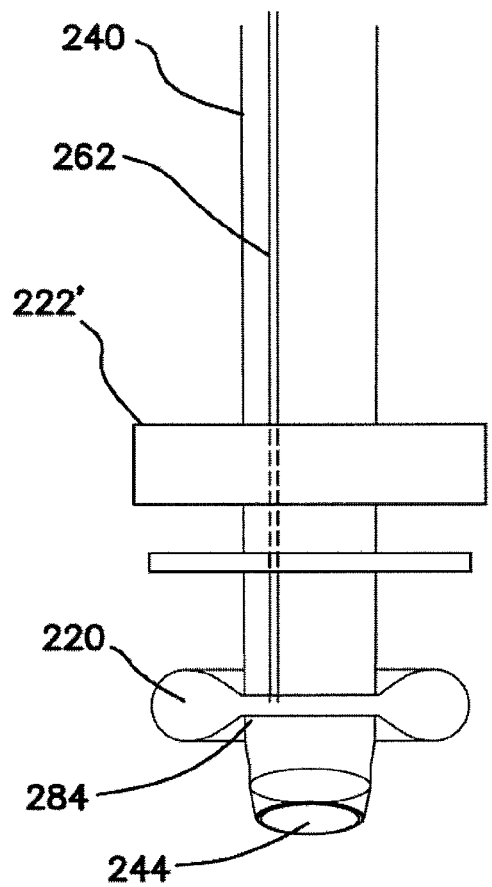
FIG. 23 schematically illustrates a distal end of an embodiment of trocar cannula assembly in a partially-assembled configuration.

Once the sleeve is locally heated 412, an inflation fluid is applied 418 to the sleeve 218 to form a balloon adjacent the distal end of the sleeve 218 proximal the bonding. FIG. 23 schematically illustrates formation of the balloon 220. In some embodiments, the balloon can be formed in a generally circular disc shape. In other embodiments, the balloon can be formed in a generally toroidal or donut shaped balloon. In other embodiments, the balloon 220 can be formed having other geometries, such as a generally frusto-conical profile or another rounded profile. Advantageously, this control in balloon shape can maximize the total working distance of the device. Furthermore, the round balloon shape and soft material provides an atraumatic means to hold the trocar assembly 210 in place.

Figure 24:
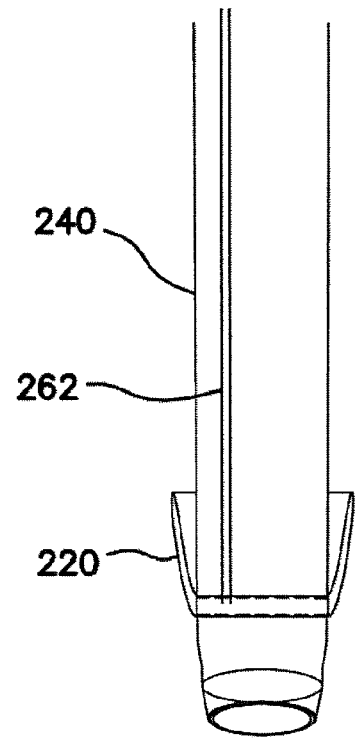
FIG. 24 schematically illustrates a distal end of an embodiment of trocar cannula assembly in a partially-assembled configuration with a balloon in a deflated state.
Figure 30:
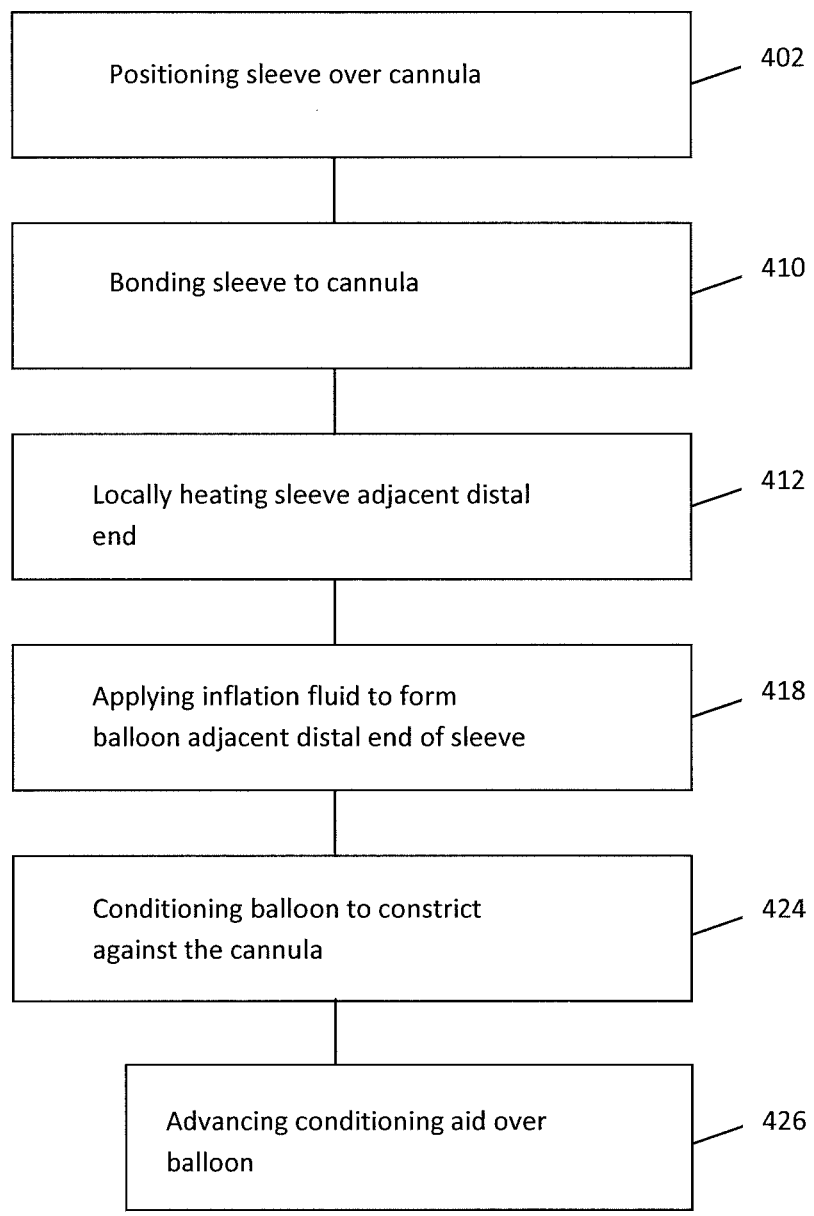
FIG. 30 illustrates an embodiment of a method for manufacturing a trocar cannula assembly.

Once the balloon is formed, the balloon can be conditioned 424 to constrict against the cannula. For example, as illustrated in FIG. 24, the balloon 220 can be folded along the elongate tubular body 282 of the sleeve 218 towards the proximal end 230 of the cannula 216 into an insertion configuration. As described above, significant reductions in insertion force can be achieved by folding the balloon in a two step process (an initial distal tuck or fold followed by a second proximal tuck or fold while the balloon retains residual heat). Desirably, the balloon can be conditioned 424 when the balloon retains heat from the local heating to enhance the constriction of the balloon. As illustrated in FIG. 30, in some embodiments, the conditioning aid 224 can then be advanced 426 over the balloon 220 to keep the balloon 220 folded until use and to retain a smooth transition from cannula distal tip 244 to balloon 220. FIGS. 25 and 26 schematically illustrate such conditioning with a conditioning aid. The interior surface of the conditioning aid 224 desirably has an inner diameter D3 sized to constrict the balloon 220 against the cannula body 240.

In some embodiments, at final sleeve sub assembly 214 configuration (FIG. 13), the retention disc 222 is placed relatively close to the distal end 232 of the cannula 216 with the conditioning aid 224 flushed against it. The retention disc 222 acts as an anchor and prevents the conditioning aid 224 from sliding proximally past the balloon 220 prior to use. Similarly, with a position adjacent the distal end 232 of the cannula 216, the retention disc 222 can be placed at a relatively small diameter of the cannula body 240 to avoid stretching the inner diameter prior to use.

Various balloon 220 folding techniques can be used to provide a relatively low diametric profile to reduce insertion force for the trocar cannula assembly. For example, in some embodiments, the balloon 220 can be folded proximally upon itself in a single folding step. Using a conditioning aid 224, the balloon 220 can be pushed against or towards a retention disk 222 or bolster 222' causing the balloon 220 to fold upon itself in a proximal direction. In other embodiments, as described further below, the balloon 220 can be folded in a two-step process with an initial distal fold followed by a proximal fold. The balloon folding technique to be incorporated in a method of manufacture for a trocar cannula assembly can be selected to provide a desired insertion force and ease of manufacturability. Desirably, further reductions in insertion force can be achieved if the two-step folding process is performed when the balloon is in a formable state.

In some embodiments, subsequent to or during the extraction of air, the retention disk 222 or bolster 222' of the trocar without a sleeve or cone (e.g., the bolster base) can be slid or pushed against a proximal end of the balloon 220 to push or apply a force distally away from the proximal end 230 of the trocar cannula 216. The distal end 306 of the bolster can be positioned adjacent the proximal end 308 of the balloon 220, as illustrated schematically in FIG. 25. Using a conditioning aid 224, the balloon 220 is pushed against or towards the retention disk 222 or bolster 222' causing the balloon 220 to fold upon itself in a proximal direction. A compressive force of the conditioning aid 224 against the balloon 220 continues as the conditioning aid 224 slides over the balloon 220. This sliding movement fully compresses the balloon 220 into a preferred, compressed condition, as illustrated schematically in FIGS. 25 and 26. The conditioning aid 224 can be advanced using a linear motion or a slight twisting motion to provide a relatively low balloon insertion profile. The retention disk 222 or bolster can be moved proximally when the conditioning aid 224 is in place covering the entire folded balloon 222. Placement of the conditioning aid 224 over the balloon 220 and in particular over the fold in the balloon 220 maintains the fold in the balloon 220 and/or the evacuation of air from the balloon 220. In one embodiment, a removable base support is removably attached to the cannula 216 and used as a support to push the proximal end of the balloon 220.

Figure 27:
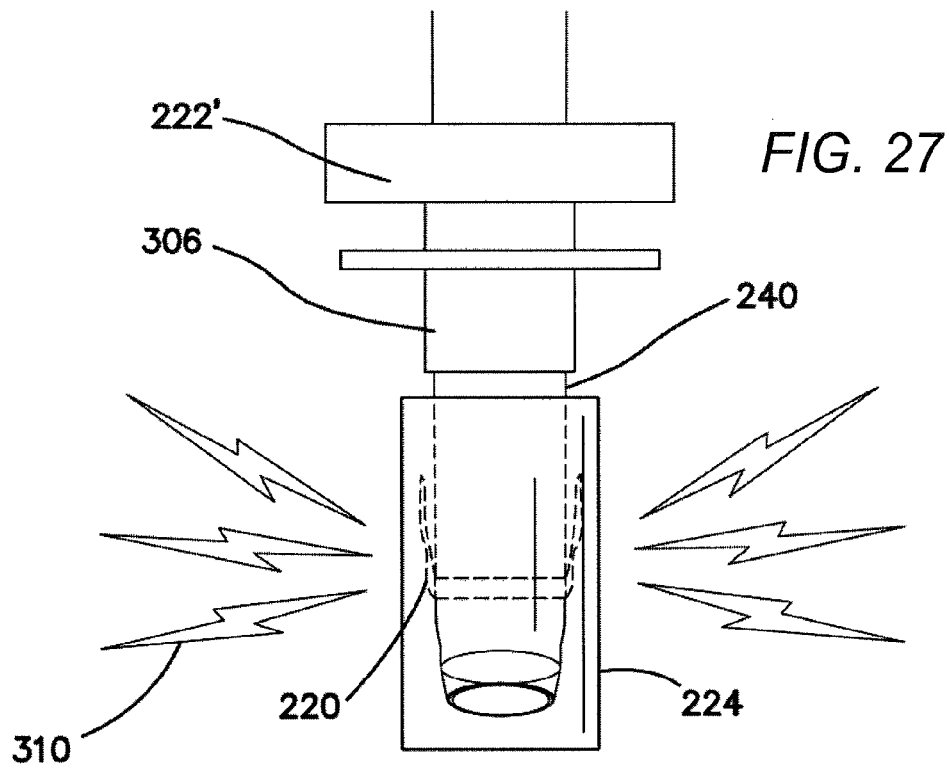
FIG. 27 schematically illustrates a distal end of an embodiment of trocar cannula assembly in a partially-assembled configuration undergoing a sterilization process.
Figure 28:
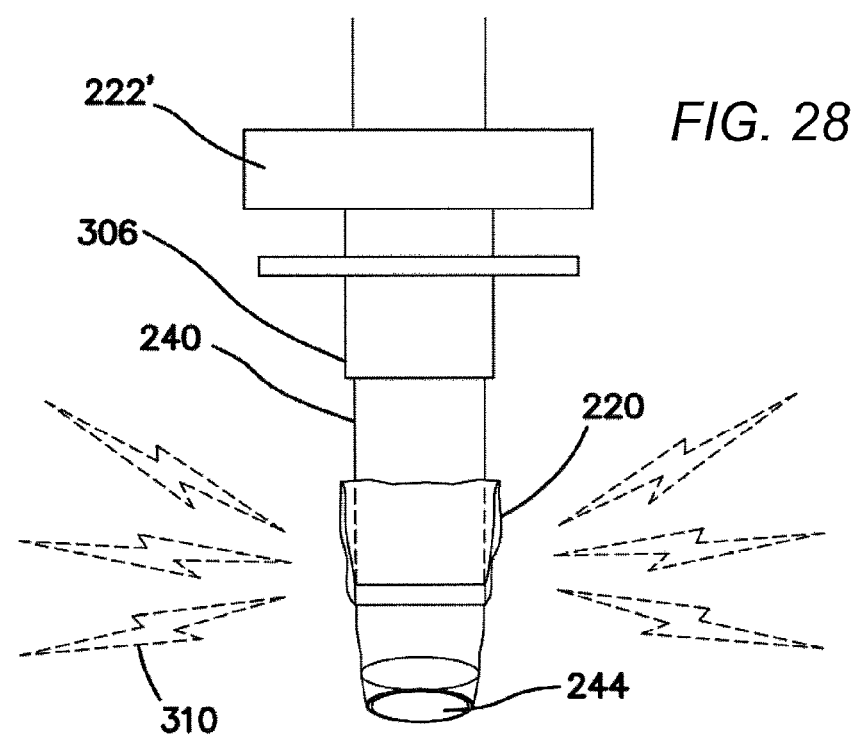
FIG. 28 schematically illustrates a distal end of an embodiment of trocar cannula assembly in a partially-assembled configuration with a balloon in a folded insertion configuration.

As illustrated schematically in FIG. 27-28, subjecting or applying sterilization 310 to the balloon 220, e.g., applying gamma sterilization to the balloon 220 further maintains the balloon 220 folded against the cannula 216 and further reduces the outer profile of the balloon 220 to be flushed or flattened against or towards the outer surface of the cannula 216. The resulting inflation configuration of the balloon 220 is illustrated schematically in FIG. 28.

The sterilization 310 process in certain embodiments may include electron-beam, gamma radiation or heat. The irradiation provides a "setting" of the folded material to a predetermined condition, size and shape. The material of the compressed balloon 220 may be partially cross-linked during this process. In the instance where heat may be applied, a heat-shrinkable material may be used for the sleeve 218 thereby compressing the balloon 220 without the friction associated with sliding a snug fitting conditioning aid 224 over the un-inflated balloon. The irradiation process 220, in one embodiment, may involve a sterilization process in which the assembled trocar cannula 216 and sleeve 218 with balloon 220 are sterilized for surgical use.

Vacuum, syringes or other air evacuation devices can be used to remove the fluid from the balloon. In one embodiment, a cap can cover the check-valve 228 of the trocar cannula assembly 210 to facilitate maintenance of the evacuation of fluid from the balloon 220 and to prevent seeping of ambient air into the balloon 220. Compression or restriction of the balloon 220 by the conditioning aid 224 facilitates maintenance of the evacuation of air and to prevent seeping of ambient air into the balloon 220. As a balloon trocar cannula assembly 210 may be turned and torqued against the body cavity or incision during use, a balloon 220 may rupture. The folding of the balloon 220 does not increase the likelihood of balloon 220 rupture and prevents potential damage to the balloon 220 during insertion. In one embodiment, further application of the syringe or other air evacuation devices to remove air from the balloon are applied while the conditioning aid 224 is placed or remains on the balloon 220, during and/or after sterilization and/or prior to removal of the conditioning aid 224.

Figure 31:
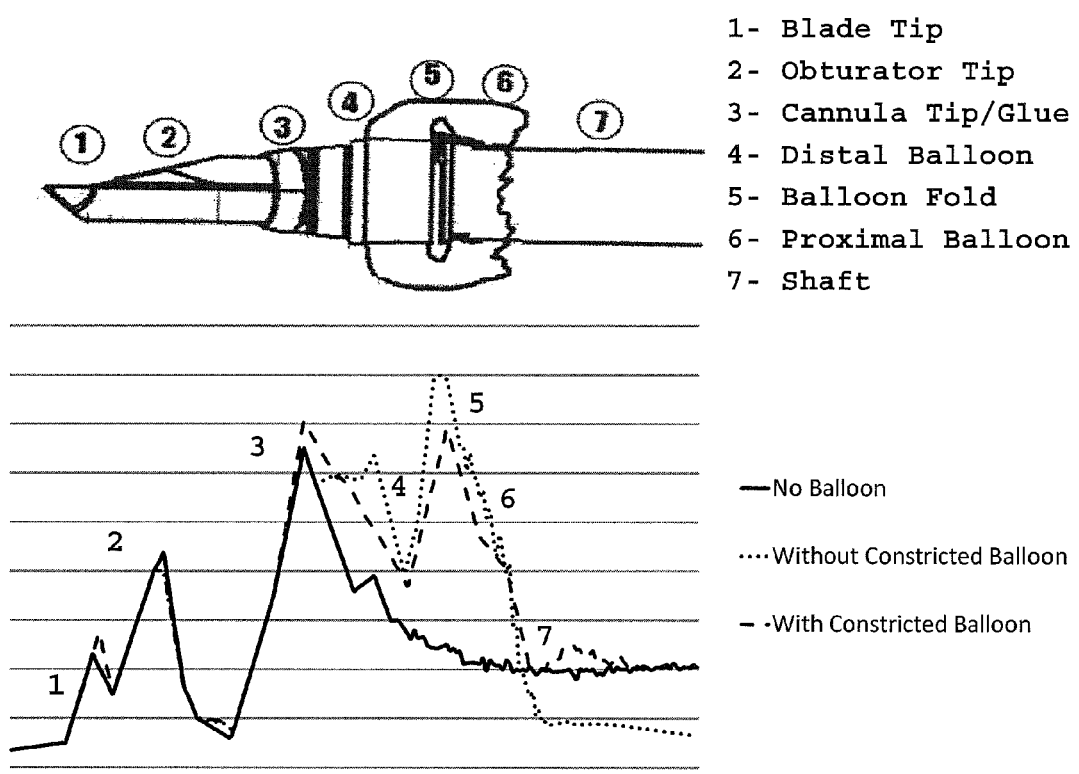
FIG. 31 illustrates an exemplary graph of an insertion force in pounds versus insertion depth for various trocar cannulae.

With reference to FIG. 31, as illustrated, some embodiments of balloon trocar including a conditioning aid 224 applied while the balloon was in a formable state (plotted as a dotted line) can have a reduced insertion force profile as compared with an equivalent balloon trocar having a balloon formed without a conditioning aid (plotted as a solid line). FIG. 31 illustrates insertion force versus insertion depth (as compared with reference positions along the cannulae, illustrated schematically above the plotted insertion force profiles) of various exemplary balloon trocar cannulae. The lightened line illustrates a reduction in insertion force local maxima or 'peaks' for an exemplary trocar cannula assembly having a balloon with a chamfered leading edge 298 and formed with a conditioning aid 224 as further discussed herein as compared with an exemplary balloon trocar cannula without these aspects. For example, at reference position 5 a local insertion force maximum can be reduced by a balloon formed with a conditioning aid. It is contemplated that certain advantageous reductions in insertion force maxima can be achieved by a balloon trocar cannula having one or both of these aspects.

Although this application discloses certain preferred embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above, but should be determined only by a fair reading of claims which follow.

What is claimed is:

1. A cannula assembly comprising:
   a cannula having a proximal end, a distal end opposite the proximal end, and a lumen extending from the proximal end to the distal end along a longitudinal axis, the lumen configured to receive a surgical instrument therein, the cannula comprising:
   a generally tubular cannula body having an exterior surface and a first outer diameter; and
   an annular recess formed in the exterior surface of the cannula body adjacent the distal end of the cannula, the annular recess transverse to the longitudinal axis, the annular recess having a second outer diameter smaller than the first outer diameter of the cannula body; and a sleeve having a proximal end and a distal end, the sleeve disposed around the cannula from adjacent the proximal end of the cannula to the annular recess, the sleeve comprising:
  an elongate tubular body;
  a balloon positioned distal the elongate tubular body; and
  a chamfered leading edge at the distal end of the sleeve; and wherein the distal end of the sleeve is coupled to the annular recess of the cannula body at a low profile transition.

2. The cannula assembly of claim 1, wherein the sleeve further comprises a bonding segment distal the balloon.

3. The cannula assembly of claim 2, wherein the bonding segment defines a longitudinal axis, and wherein the chamfered leading edge defines an angle of between approximately 50 degrees and approximately 65 degrees relative to the longitudinal axis of the bonding segment.

4. The cannula assembly of claim 1, wherein the annular recess has a textured surface.

5. The cannula assembly of claim 1, wherein the sleeve is monolithically unitarily formed.

6. The cannula assembly of claim 1, further comprising a conditioning aid removably disposed around the balloon.

7. The cannula assembly of claim 1, further comprising an adhesive substantially within the annular recess to couple the distal end of the sleeve to the annular recess.

8. The cannula assembly of claim 7, wherein the distal end of the sleeve is positioned in the annular recess to define an exposed segment of the annular recess, the exposed segment sized to receive the adhesive.

9. The cannula assembly of claim 1, wherein the elongate tubular body has a first thickness, and the balloon has a second thickness smaller than the first thickness.

* * * * *